United States Patent
Brenna et al.

(10) Patent No.: US 9,914,969 B2
(45) Date of Patent: Mar. 13, 2018

(54) FADS REGULATION

(71) Applicant: CORNELL UNIVERSITY, Ithaca, NY (US)

(72) Inventors: James Thomas Brenna, Ithaca, NY (US); Holly Turner Reardon, Santee, CA (US); Sesha Durga Kumar Kothapalli, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 61 days.

(21) Appl. No.: 14/376,410

(22) PCT Filed: Jan. 28, 2013

(86) PCT No.: PCT/US2013/023507
§ 371 (c)(1),
(2) Date: Aug. 1, 2014

(87) PCT Pub. No.: WO2013/113030
PCT Pub. Date: Aug. 1, 2013

(65) Prior Publication Data
US 2015/0018378 A1    Jan. 15, 2015

Related U.S. Application Data

(60) Provisional application No. 61/591,064, filed on Jan. 26, 2012.

(51) Int. Cl.
*C12Q 1/68* (2006.01)
*A61K 31/366* (2006.01)
*A61K 31/7048* (2006.01)
*A61K 38/31* (2006.01)
*A61K 31/505* (2006.01)
*A61K 31/18* (2006.01)
*A61K 31/195* (2006.01)
*A61K 31/22* (2006.01)
*A61K 31/40* (2006.01)
*A61K 31/404* (2006.01)
*A61K 31/575* (2006.01)

(52) U.S. Cl.
CPC ............ *C12Q 1/6883* (2013.01); *A61K 31/18* (2013.01); *A61K 31/195* (2013.01); *A61K 31/22* (2013.01); *A61K 31/366* (2013.01); *A61K 31/40* (2013.01); *A61K 31/404* (2013.01); *A61K 31/505* (2013.01); *A61K 31/575* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 6,825,017 B1 | 11/2004 | Browse et al. | |
| 2010/0099901 A1 | 4/2010 | Hayashi et al. | |
| 2011/0112186 A1* | 5/2011 | Link | C12Q 1/6883 514/460 |
| 2011/0191906 A1 | 8/2011 | Ohyama | |
| 2011/0301186 A1* | 12/2011 | Levy | A61K 31/355 514/275 |

FOREIGN PATENT DOCUMENTS

| CN | 101200728 A | 6/2008 |
| EP | 1035207 A1 | 9/2000 |
| WO | 0021557 A1 | 4/2000 |
| WO | 2013113030 A1 | 8/2013 |

OTHER PUBLICATIONS

NCBI SNP Database for rs66698963, ss101754891, available online May 18, 2008, available via url: <ncbi.nlm.nih.gov/projects/SNP/snp_ss.cgi?subsnp_id=101754891>.*
Reardon et al Prostaglandins Leukot Essent Fatty Acids. Jun. 27, 2012. 87(1): 25-33.*
Goldstein, M.R. Current Oncology. 2008. 15(2): 76-77.*
Ravnskov et al (J Clin Oncology. Jan. 20, 2015. vol. 33, pp. 1-3.*
van der Vaart et al. The Lancet Neurology. Nov. 2013. 12(11): 1076-1083.*
Gagneux et al. Molecular Phylogenetics and Evolution. 2001. 18: 2-13.*
Halushka et al. Nature. Jul. 1999. 22: 239-247.*
NCBI dbSNP rs138766446, ss327344667, Mar. 11, 2011. National Center for Biotechnology Information, National Library of Medicine (Bethesda, MD, USA).*
Boker et al J. Lipid Research. 2010. 51: 2325.*
Nwankwo, J. 0. et al., "A nucleotide insertion in the transcriptional regulatory region of FADS2 gives rise to human fatty acid delta-6-desaturase deficiency" , Journal of Lipid Research, 2003, vol. 44, pp. 2311-2319 . See the whole document.
Sun Lin, et al., "Association analysis between polymorphisms of FADS1/Fads 2 gene and coronary heart disease", Journal of Jilin University (Medicine Edition), Jan. 2012, vol. 38, pp. 115-118.

* cited by examiner

*Primary Examiner* — Carla J Myers
(74) *Attorney, Agent, or Firm* — Jun He Law Offices P.C.; James J. Zhu

(57) ABSTRACT

The present invention relates methods to increase the expression of fatty acid desaturases (FADS) and increase cellular and tissue levels of highly unsaturated fatty acids (HUFA) by modulating one or more of the FADS via the action of specific classes of drugs (e.g., statins and LXR agonists). The present invention also relates to methods of treating conditions (e.g., tumor and cancer) involving deficient function of FADS by administering statins and/or LXR agonists. The present invention further relates to methods of determining the need for statins or dietary LCPUFA in subjects.

13 Claims, 11 Drawing Sheets

A
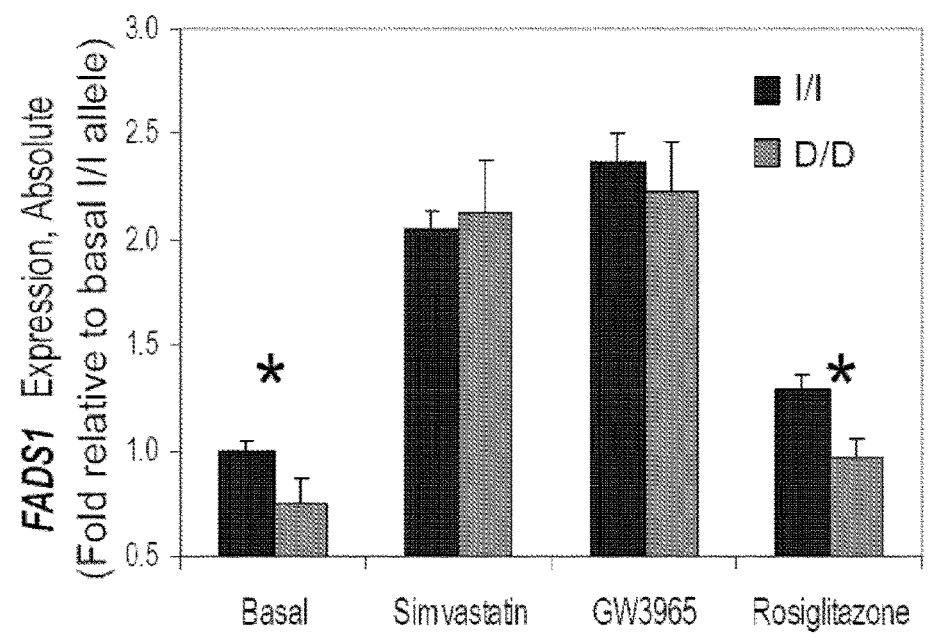
C
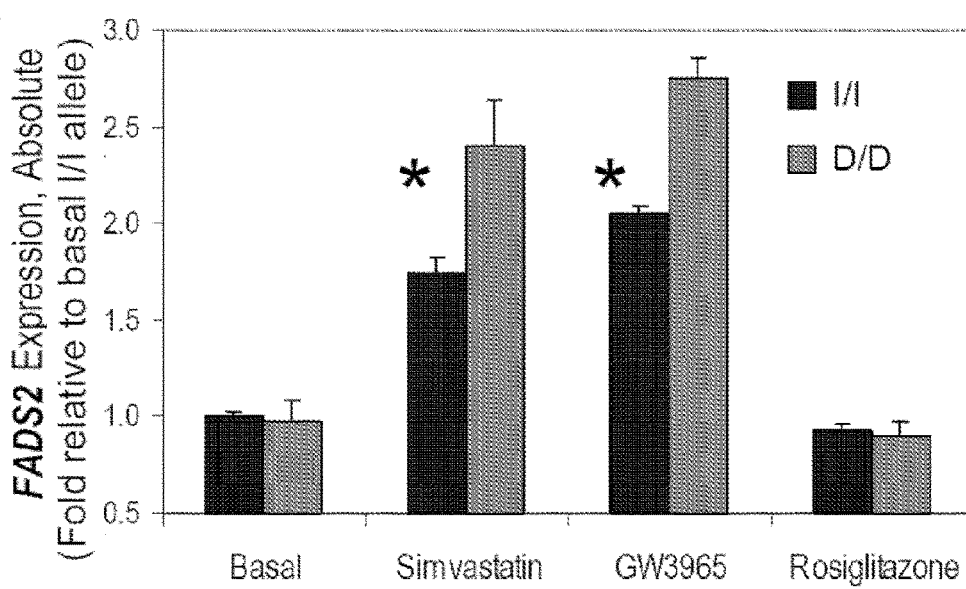
Figure 4

Lane 1: 100 bp Ladder; Lanes 2, 3, 5: I/D genotype; Lane 4: D/D genotype; Lane 6: I/I genotype.

A). Intron 1 fragment containing Insertion I (SEQ ID NO: 3)

Nucleotide No. of SEQ ID NO: 2      0 | 1           50 | 51    72 | 73           122
                                      | C            G | A     G | C              T B). Intron 1 fragment lacking Insertion I (SEQ ID NO: 3)

Nucleotide No. of SEQ ID NO: 2      0 | 1           50 | 73                       122
Nucleotide No. of SEQ ID NO: 3      0 | 1           50 | 51                       100
                                      | C            G | C                         T C). Intron 1 fragment containing Insertion II (SEQ ID NO: 4)

Nucleotide No. of SEQ ID NO: 4      0 | 1           50 | 51    53 | 54            103
                                      | C            C | C     A | C               A
                                                         52 | 53
                                                          C | A D). Intron 1 fragment lacking Insertion II (SEQ ID NO: 5)

Nucleotide No. of SEQ ID NO: 4      0 | 1           50 | 54                       103
Nucleotide No. of SEQ ID NO: 5      0 | 1           50 | 51                       100
                                      | C            C | C                         A E). Intron 1 fragment lacking Insertion III (SEQ ID NO: 6)

Nucleotide No. of SEQ ID NO: 4      0 | 1           52 | 54                       103
Nucleotide No. of SEQ ID NO: 6      0 | 1           52 | 53                       102
                                      | C            C | C                         A

Figure 8

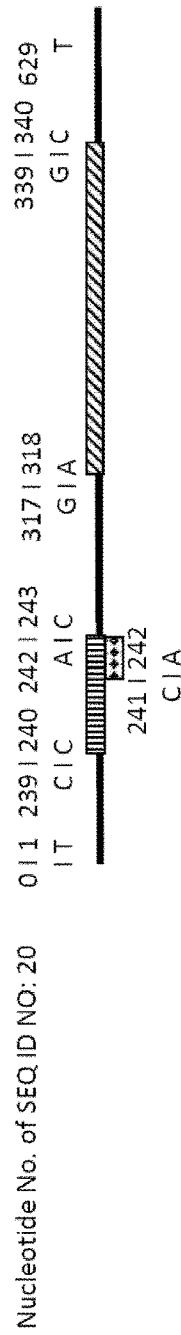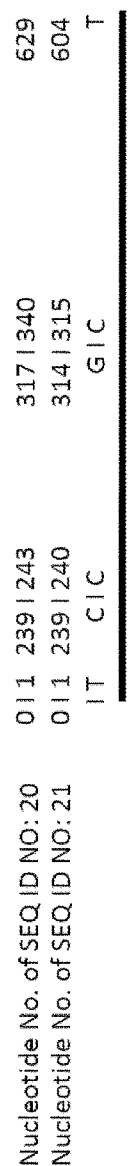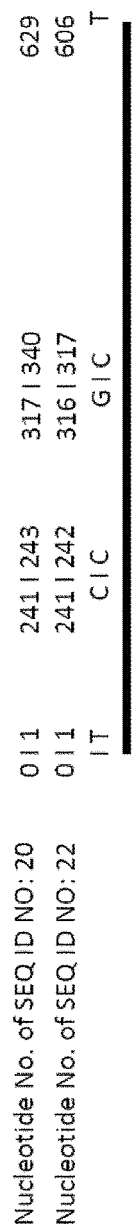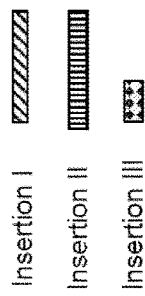
Figure 9

FADS REGULATION

CROSS-REFERENCE TO RELATED APPLICATIONS

The present application is the national stage of International Application PCT/US2013/023507, filed Jan. 28, 2013, which claims the benefit of U.S. Provisional Patent Application No. 61/591,064, filed on Jan. 26, 2012, the disclosure of which is incorporated herein by reference in their entirety. The invention herein was made in the course of work under a grant from the United States Department of Health and Human Resources.

GOVERNMENT LICENSE RIGHTS

This invention was made with US government support under Grant Number 5T32HD052471 awarded by National Institutes of Health. The government has certain rights in the invention.

FIELD OF INVENTION

The present invention relates to the field of modulation of fatty acid desaturases (FADS) expression and the application thereof in disease treatment.

BACKGROUND

The delta-5 and delta-6 desaturases (encoded by FADS1 and FADS2, respectively) are essential for biosynthesis of long-chain omega-3 and omega-6 fatty acids. These long-chain polyunsaturated fatty acids (LCPUFA), such as docosahexaenoic acid (DHA) and arachidonic acid (ARA), are major components of cell membranes in the central nervous system, act as precursors for signaling molecules such as eicosanoids and docosanoids, and directly affect gene expression to influence important physiological functions such as inflammation and blood clotting[1-3]. Although both ARA and DHA can be obtained pre-formed through diet, most populations do not consume enough to completely remove any dependence on biosynthesis. Indeed, genetic studies have underscored the importance of FADS1 and FADS2 by linking single nucleotide polymorphisms (SNPs) in these genes with numerous health outcomes, including coronary artery disease, total cholesterol, LDL, C-reactive protein levels, allergy and atopic eczema, as well as cognitive outcomes such as attention-deficit hyperactivity disorder and IQ in children[4-9].

However, mechanisms describing how gene variants affect FADS gene function are lacking, so it is difficult to translate polymorphism associations into disease prevention or treatment. Despite numerous Polymorphisms in FADS2 associated with health outcomes, there are no validated non-synonymous Polymorphisms in the FADS2 gene. This suggests that mechanisms are likely to be regulatory rather than through protein structural changes for any causal Polymorphisms in FADS2. A causal polymorphism in the promoter region of FADS2 has been reported[10], but this polymorphism is not polymorphic in the Han Chinese, Japanese, and Yoruba International HapMap project populations (HapMap Genome browser release #28). Thus, this one polymorphism does not explain all associations found in other world populations. In addition, this polymorphism only affects FADS2 expression, so it does not explain results in European or majority European-descendent populations suggesting lower Δ5-desaturase activity associated with some Polymorphisms[11-13].

Some key molecules involved in regulation of FADS1 and FADS2 gene expression have been identified, but regulatory regions and functional binding sites within these genes have not been fully elucidated. The FADS genes reside as a cluster on chromosome 11 consisting of FADS1, FADS2 and a third putative desaturase designated FADS3. All reported mechanisms for regulation, such as dietary fatty acid or hormonal responses, affect both FADS1 and FADS2 in concert. For example, the end-product DHA is known to down-regulate expression of both FADS1 and FADS2 by lowering activity of the sterol response element binding protein 1c (SREBP-1c)[14]. Other transcription factors that have been implicated in regulation of FADS genes include the peroxisome proliferator-activated receptors (PPARs)[15]. However, no information is available to link specific Polymorphisms and phenotypes with response to specific transcription factors.

Therefore, there exists a great need to identify proper subjects of certain polymorphisms, better modulate FADS expression in these subjects, and hence better regulate biosynthesis of LCPUFA therein.

SUMMARY OF THE INVENTION

One aspect of the present disclosure related to methods of modulating or treating a condition involving deficient function of FADS in a subject, comprising identifying the absence of an Insertion in intron 1 of FADS2 gene in the subject, and administering a therapeutically effective amount of at least one FADS-modulating agent to the subject.

In certain embodiments, an Insertion disclosed herein include: 1) Insertion 1 (SEQ ID NO. 1) having a nucleotide sequence of "ACTTCTCCCTGCCTCCCCAGGG") at rs66698963, which resides at nucleotides numbers. 51-72 of a sequence as shown in SEQ ID No. 2; 2) Insertion II having a nucleotide sequence of CCA at rs138766446 which resides at nucleotides numbers 51-52 of a sequence as shown in SEQ ID No. 4; and 2) Insertion III having a single nucleotide adenosine (A) at rs149597144 which resides at nucleotide number 53 of a sequence as shown in SEQ ID NO. 4.

In certain embodiments, the Insertion is Insertion I, Insertion II, Insertion III, a combination of Insertion I and Insertion II, or a combination of Insertion I and Insertion III.

In certain embodiments, FADS include FADS1 and FADS2. In certain embodiments, FADS include FADS2.

In certain embodiments, the FADS-modulating agent is an SREBP-1c agonist. In certain embodiments, the FADS-modulating agent is a statin or LXR agonist. In certain embodiments, the FADS-modulating agent is not a PPARγ agonist. For example, a statin drug is simvastin, atorvastatin, mevacor, fluvastatin, lovastatin, pravastatin, or rosuvastatin. For another example, an LXR agonist is GW3965, hypocholamide, T0901317, or N,N-dimethyl-3beta-hydroxycholenamide.

In certain embodiments, the condition involving deficient function of FADS is tumor or cancer. In certain embodiments, the condition is tumor development, angiogenesis or metastasis.

In certain embodiments, the agent can be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

Another aspect of the present disclosure relates to methods of increasing the cellular concentration of highly unsaturated fatty acids (HUFA), comprising identifying the absence of an Insertion in intron 1 of FADS2 gene in the cell, providing to the cell at least one FADS-modulating agent. In certain embodiments, the Insertion is Insertion I, Insertion II, Insertion III, a combination of Insertion I and Insertion II, or a combination of Insertion I and Insertion III.

Another aspect of the present disclosure relates to a method of restoring intercellular signaling in a cell, comprising identifying the absence of an Insertion in intron 1 of FADS2 gene in the cell, providing least one FADS-modulating agent to the cell. In certain embodiments, the cell is a tumor cell or a cancer cell.

Another aspect of the present disclosure relates to pairs of isolated oligonucleotide 5' primer and 3' primer, in which amplification of the pair of primers is indicative of the absence of presence of an Insertion in intron 1 of FADS2 gene, in which the insertion is Insertion I, Insertion II, or Insertion III.

Another aspect of the present disclosure relates to an oligonucleotide probe capable of selectively hybridizing to a fragment of intron 1 of FADS2 gene containing Insertion I, Insertion II, or Insertion III but not a fragment lacking Insertion I, Insertion II, or Insertion III.

Another aspect of the present disclosure relates to an oligonucleotide probe capable of selectively hybridizing to a fragment of intron 1 of the FADS2 gene lacking Insertion I, Insertion II, or Insertion III but not a fragment containing Insertion I, Insertion II, or Insertion III.

Another aspect of the present disclosure relates to kits comprising a pair of primers provided herein, a primer provided herein or an oligonucleotide probe provided herein.

Another aspect of the present disclosure relates to a method of determining the need for FADS-modulating agent or dietary long chain polyunsaturated fatty acids (LCPUFA) in a subject by determining the presence or absence of Insertion I, Insertion II, and Insertion III in a subject, whereas the absence of at least one of the insertions is an indication of the need for FADS-modulating agent and/or dietary LCPUFA.

In certain embodiment, the presence of SEQ ID NO. 3 and/or the presence of SEQ ID NO. 5 (or SEQ ID NO. 6) in a subject indicate the need for FADS-modulating agent and/or dietary LCPUFA. In certain embodiment, the presence of SEQ ID NO. 3 but not SEQ ID NO. 2, and/or the presence of SEQ ID NO. 5 but not SEQ ID NO. 4, indicate the need for FADS-modulating agent and/or dietary LCPUFA. In certain embodiments, the presence of SEQ ID NO. 3 but not SEQ ID NO. 2, and/or the presence of SEQ ID NO. 6 but not SEQ ID NO: 4, indicate the need for FADS-modulating agent and/or dietary LCPUFA.

BRIEF DESCRIPTION OF THE DRAWINGS

FIG. 8. Schematic drawings showing the Insertions or the absence of Insertions in SEQ ID NOs: 2-6 in the intron 1 region of the FADS 2 gene.

FIG. 9. Schematic drawings showing the Insertions or the absence of Insertions in the 629-bp fragment in the intron 1 region of the FADS 2 gene.

DETAILED DESCRIPTION OF THE INVENTION

The following description is merely intended to illustrate various embodiments of the present disclosure. As such, the specific modifications discussed are not intended to be limiting. It will be apparent to one skilled in the art that various equivalents, changes, and modifications may be made without departing from the spirit or scope of the subject matters presented herein, and it is understood that such equivalent embodiments are to be included herein.

All references cited herein, including publications, patents and patent applications are incorporated herein by reference in their entirety.

Polymorphisms and Treatments

One aspect of the present disclosure relates to methods of modulating or treating a condition involving deficient function of a fatty acid desaturase (FADS) gene in a subject, comprising identifying the absence of an Insertion in intron 1 of the FADS2 gene in a subject, and administering a therapeutically effective amount of at least one FADS-modulating agent to the subject.

The term "the FADS gene" as used herein, refers to a gene that encodes for a fatty acid desaturase, for example but mot limited to, delta-5 and delta-6 desaturases, which are essential for biosynthesis of long-chain omega-3 and omega-6 fatty acids. The FADS gene may include FADS1, FADS2, and FADS3. In certain embodiments, FADS gene includes the FADS1 gene and the FADS2 gene. FADS1 and FADS2 are isoforms of FADS genes. FADS1 encodes for delta-5 desaturases and FADS2 encodes for delta-6 desaturases.

Figure 5:
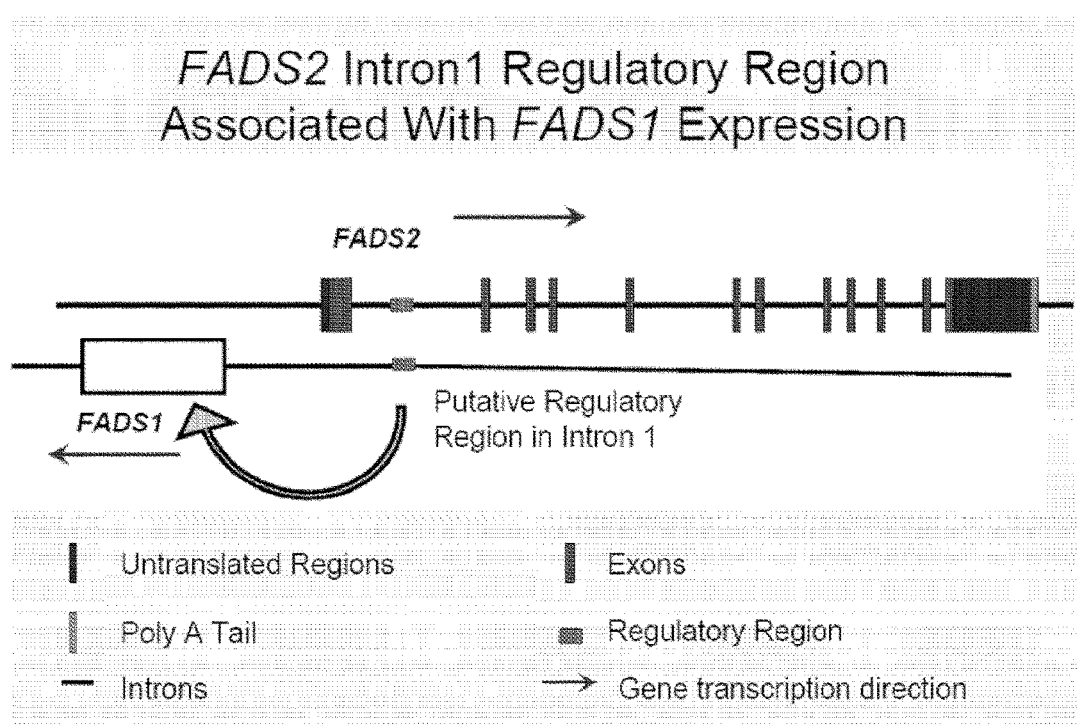
FIG. 5. FADS1 and FADS2 are oriented in a head-to-head configuration on the long arm of human chromosome 11. It shows how the regulatory region that includes the indel serves as a common bidirectional regulator. There is a precedent for other genes regulated in this manner (See Ueda et al, 2006 (Ref#25)).

The term "intron 1 of the FADS2 gene" as used herein refers to the first intron which is closest to the transcription initiation site of the FADS2 gene. Intron 1 of the FADS2 gene is positioned between exons 1 and 2 of the FADS2 gene. The FADS2 gene is positioned immediately adjacent at a distance of 11.3 kb to FADS1 in a head-to-head orientation on the long arm of human chromosome 11 (See FIG. 5)[24], so that intron 1 of the FADS2 gene is upstream of the transcription start site for FADS1.

As used herein, the term "Insertion" refers to a nucleotide sequence fragment (having one or more nucleotides) which is found to be present at a specific site of the genome of one subject (or one allele of the subject), but is absent at the identical site of the genome of another subject (or the other allele of the subject). For a subject or an allele lacking an "Insertion," it may also be referred to as having a deletion, i.e. having the insertion deleted. An insertion can be present in a genomic DNA sequence, an RNA transcript, or an mRNA. An insertion may possibly be found in a functional region such as an intron, an exon, or in a regulatory region such as a promoter of a gene. An insertion can be a single nucleotide, or more than one nucleotide (e.g. 2 nucleotides, 3 nucleotides, 10s nucleotides, or even 100s nucleotides).

In certain embodiments, the absence of an Insertion in intron 1 of FADS2 gene is identified in a subject. By "absence of an Insertion," it is meant to refer to absence of such insertion in at least one allele of a subject. For example, for a human subject, it is possible that the subject has one allele lacking the insertion, but the other allele having the insertion. Alternatively, the subject may have both alleles absent of the insertion. Typically, symbol "−/−" or "D/D" is usually used to indicate for a subject whose both alleles lack the insertion, and such a subject is referred to herein as "homozygous for insertion"; symbol "+/+" or "I/I" is usually used to indicate for a subject whose both alleles contain the insertion, and such a subject is referred to herein as "homozygous for deletion"; and symbol "+/−" or "I/D" is usually used to indicate for a subject in which one allele contains the insertion, and the other allele lacks the insertion, and such a subject is referred to herein as "heterozygous for insertion/deletion".

In certain embodiments, the Insertion in the present disclosure is Insertion I, Insertion II, Insertion III, a combination of Insertion I and Insertion II, or a combination of Insertion I and Insertion III.

As used herein, the term "Insertion I" refers to "ACTTCTCCCTGCCTCCCCAGGG" (SEQ ID NO. 1) at rs66698963 resides at nucleotides numbers. 51-72 of a sequence as shown in SEQ ID No. 2. Insertion II refers to a nucleotide sequence of CCA at rs138766446 which resides at nucleotides numbers 51-52 of a sequence as shown in SEQ ID No. 4. Insertion III refers to a single nucleotide adenosine (A) at rs149597144 which resides at nucleotide number 53 of a sequence as shown in SEQ ID NO. 4.

In an illustrative embodiment, for a subject homozygous for Insertion I, the intron 1 of FADS2 gene comprises the following sequence, in which Insertion I is underlined:

rs66698963 (+/+): SEQ ID NO. 2
CCAGGGCCTCCTCCCTGCCTCCCCAGGGACTTCTCCCTGCCTCCC*AGGG*

*ACTTCTCCCTGCCTCCCCAGGGCCCT*GGAATAGCACGTCTCTTTTCCCTG

AAAATACTCTTGACCTGATCCT.

In another illustrative embodiment, for a subject homozygous for deletion of Insertion I, the intron 1 of FADS2 gene comprises the following sequence, in which Insertion I is shown as "−":

rs66698963 (−/−): SEQ ID NO. 3
CCAGGGCCTCCTCCCTGCCTCCCCAGGGACTTCTCCCTGCCTCCC*AGGG*

*CCCT*GGAATAGCACGTCTCTTTTCCCTGAAAATACTCTTGACCTGATCCT.

In an illustrative embodiment, for a subject homozygous for Insertion II, the intron 1 of FADS2 gene comprises the following sequence, in which Insertion II is underlined:

rs138766446 (+/+): SEQ ID NO. 4
CCCTGGGCTCCTCCCTGCCCGCACCCTGGGCCTCCTCCCTGCCTGC*CCCC*

CC*ACCCC*AGCCCTCCTCCCTGCCTGCCCCAGGGCCTCCTCCCTGCCTCC

CCA.

In another illustrative embodiment, for a subject homozygous for deletion of Insertion II, the intron 1 of FADS2 gene comprises the following sequence, in which Insertion II is shown as "−":

rs138766446 (−/−): SEQ ID NO. 5
CCCTGGGCTCCTCCCTGCCCGCACCCTGGGCCTCCTCCCTGCCTGC*CCCC*

*CCCC*AGCCCTCCTCCCTGCCTGCCCCAGGGCCTCCTCCCTGCCTCCCCA.

In an illustrative embodiment, for a subject homozygous for Insertion III, the intron 1 of FADS2 gene comprises the following sequence, in which Insertion III is underlined:

```
rs138766446 (+/+): SEQ ID NO. 4
CCCTGGGCTCCTCCCTGCCCGCACCCTGGGCCTCCTCCCTGCCTGCCC

CCCCACCCCAGCCCTCCTCCCTGCCTGCCCCAGGGCCTCCTCCCTGC

CTCCCCA.
```

In another illustrative embodiment, for a subject homozygous for deletion of Insertion III, the intron 1 of FADS2 gene comprises the following sequence, in which Insertion III is shown as "–":

```
rs149597144 (-/-): SEQ ID NO. 6
CCCTGGGCTCCTCCCTGCCCGCACCCTGGGCCTCCTCCCTGCCTGCCC

CCCCCCCAGCCCTCCTCCCTGCCTGCCCCAGGGCCTCCTCCCTGCC

TCCCCA.
```

In certain embodiments, the insertion is a combination of Insertion I and Insertion II, or Insertion I and Insertion III. For a subject homozygously having all the Insertions I, II, & II, the intron 1 of the FADS2 gene comprises SEQ ID NO: 20 (i.e., the 629 bp fragment from bases 6908015 to 6908643 in the sequence of GenBank Accession Number NT 167190.1). For a subject homozygous for deletion of both Insertion I and Insertion II, the intron 1 of the FADS2 gene comprises SEQ ID NO: 21. For a subject homozygous for deletion of both Insertion I and Insertion III, the intron 1 of the FADS2 gene comprises SEQ ID NO: 22. The positions of the Insertions and deletions in SEQ ID NOs: 20-22 are shown in FIG. 9 A)-C).

In certain embodiments, the present or absence of the Insertion in a subject can be identified in any suitable methods known in the art. In certain embodiments, a polymerase chain reaction (PCR) based method can be used. For example, a fragment suspected of containing the insertion may be amplified using PCR, and the amplicon may be sequenced to allow identification of the presence or absence of the insertion. The size of the amplicon may be compared to a control amplicon having the Insertion(s) to determine the presence of absence of the Insertion(s). For another example, a fragment suspected of containing the Insertion(s) may be amplified using primers capable of recognizing the Insertion(s), such that an amplicon would be selectively produced if the sample contains the Insertion(s), or vice versa. In certain embodiments, a probe-based method can be used to identify the insertion. For example, a sample suspected of containing the insertion may be subject to hybridization with a probe capable of recognizing the Insertion(s), such that hybridization occurs only if the sample contains the Insertion(s), or vice versa. For another example, a sample suspected of containing the Insertion(s) is allowed to hybridize with a probe capable of recognizing the Insertion(s), and the Tm value of the hybridization product can be detected, where the Tm would be distinguishably different for a sample containing the Insertion(s) from a sample containing not. The identification methods and reagents useful for such identification are provided in much detail below in the present disclosure.

The methods provided herein further comprise administering a therapeutically effective amount of at least one FADS-modulating agent to the subject. Without being bound to any theory, it is found that FADS2 sequence may have a regulatory function on transcription and/or expression of FADS1 and/or FADS2. The region accommodating for Insertion I, Insertion II and Insertion III in FADS2 intron 1 are found to be highly conserved from human to zebrafish, and such region is believed to contain predicted binding sites for sterol response element binding protein (SREBP) and peroxisome proliferator-activated receptor gamma (PPARγ). It is unexpectedly found that subjects lacking Insertion I, Insertion II and/or Insertion III are likely to be associated with lower basal expression of FADS1 gene, and therefore are likely to have a condition involving deficient function of FADS.

The term "deficient function of FADS" as used herein, refers to insufficient biological activity of a FADS gene. In certain embodiments, deficient function of FADS is characterized in reduced or insufficient expression of FADS gene in a subject, and/or insufficient supply of long chain polyunsaturated fatty acids (LCPUFA) in a subject, as FADS gene is responsible for biosynthesis of LCPUFA in vivo. When intake of LCPUFA from food consumption is insufficient, a subject would rely on FADS function for its biosynthesis of LCPUFA. In such case, a subject having deficient function of FADS would be at risk for insufficient supply of LCPUFA, and consequently, at risk for condition involving such insufficient supply of LCPUFA.

Exemplary conditions involving deficient function of FADS include, without limitation, coronary artery disease, total cholesterol, LDL, C-reactive protein levels, allergy and atopic eczema, as well as cognitive outcomes such as attention-deficit hyperactivity disorder and IQ in children[4-9], tumor, or cancer.

In certain embodiments, the condition is tumor or cancer. In certain embodiments, the condition is tumor development, angiogenesis or metastasis.

The conditions can be modulated or treated by the FADS-modulating agents. The term "modulating" as used herein, means alleviating, improving, protecting from, preventing, treating, reducing symptoms of, and/or curing.

The term "FADS-modulating agent" as used herein, refers to an agent capable of modulating transcription of a FADS mRNA, expression of a FADS protein, and/or biological activity of a FADS protein. In certain embodiments, the FADS-modulating agent enhances the transcription of a FADS mRNA, expression of a FADS protein, and/or biological activity of a FADS protein.

In certain embodiments, the FADS-modulating agent is a SREBP-1c agonist. SREBP is a family of transcription factors that bind to the sterol regulatory element (SRE) DNA sequence TCACNCCAC, in which N can be any nucleotide. SREBP-1c is an isoform of SREBP-1, and is associated with regulation of de novo lipogenesis. A SREBP-1c agonist is an agent that can promote the binding of SREBP-1c to the SRE DNA sequence, and/or enhance the transcription of the target gene under control of the SRE sequence via activation of SREBP-1c.

It has been unexpectedly found that, although the region accommodating for Insertion I, Insertion II and Insertion III in FADS2 intron 1 is predicted to contain both SREBP binding sites and PPARγ binding sites, SREBP-1c agonists, but not PPARγ agonists, are capable of modulating FADS activity. Moreover, SREBP-1c agonists modulates FADS activity differentially in subjects containing the insertions in FADS2 intron 1 from subjects lacking such insertions, whereas PPARγ agonists do not show any difference on those subjects.

In certain embodiments, the FADS-modulating agent is a SREBP-1c agonist but not a PPARγ agonist.

In certain embodiments, the FADS-modulating agent is a statin or a Liver X receptor (LXR) agonist. Statins are a class of drugs capable of inhibiting HMG-CoA reductase. For example, a statin drug is simvastin, atorvastatin, mevacor, fluvastatin, lovastatin, pravastatin, or rosuvastatin. For another example, an LXR agonist is GW3965, hypocholamide, T0901317, or N,N-dimethyl-3beta-hydroxy-cholenamide.

In certain embodiments, at least one FADS-modulating agent is administered. For example, one or more FADS-modulating agents are administered. For another example, the FADS-modulating agent may be administered in combination with an additional agent or dietary supplement having a rich content of LCPUFA (e.g. fish oil).

In certain embodiments, the FADS-modulating agents can be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes. Depending on the administration routes, the FADS-modulating agent can be prepared into any formulation suitable for such administration routes. For example, the FADS-modulating agents can be orally administered in solid dosage forms such as tablets and capsules. For another example, the agents can be administered in parenteral route in injections which are sterile and pyrogen free. Preparation methods for a suitable dosage form and administration thereof are well known to people skilled in the art, see, for example, Remington's Pharmaceutical Science, 15th ed., Mack Publishing Company, Easton, Pa. (1980).

The FADS-modulating agents are administered in a therapeutically effective amount. "Therapeutically effective amount" as used herein, refers to the amount of the FADS-modulating agent which is required to achieve a desired or intended physiological outcome in a subject. Therapeutically effective amount may vary among individuals, and may be determined by a physician taking into consideration of different factors such as age, gender, genotypes in FADS genes, and food intake of LCPUFA.

Another aspect of the present disclosure relates to methods of increasing the cellular concentration of LCPUFA, comprising identifying the absence of an Insertion in intron 1 of the FADS2 gene in the cell, providing to the cell at least one FADS-modulating agent, in which the insertion is a combination of Insertion I and Insertion II, or Insertion I and Insertion III. The cellular concentration of LCPUFA can be determined using any suitable methods known in the art. For example, lipids of cells can be extracted and LCPUFA analyzed by gas chromatography, or by gas chromatography/mass spectrometry, or by high performance liquid chromatography/mass spectrometry, or by electrospray mass spectrometry or by atmospheric pressure chemical ionization mass spectrometry Another aspect of the present disclosure relates to a method of restoring intercellular signaling in a cell, comprising identifying the absence of an insertion in intron 1 of the FADS2 gene in the cell, providing least one FADS-modulating agent to the cell. In certain embodiments, the cell is a tumor cell or a cancer cell.

Detection of the Insertions

Another aspect of the present disclosure relates to methods and reagents for detecting the Insertions in the intron 1 of the FADS2 gene.

Various methods are known in the art to detect for the insertion of a single nucleotide or of a multi-nucleotide fragment. Suitable methods include, for example, PCR based methods, primer extension, and probe hybridization.

PCR-Based Method

In PCR-based methods, a pair of primers may be used to amplify a DNA sequence from a subject to be determined for the presence or absence of the Insertion(s). The primers can be designed such that presence or absence of the insertion in the subject DNA sequence would be distinguished by different amplification results, for example, presence and absence of an amplicon, different size of the amplicons, and/or different nucleotide sequence at the insertion site in the amplicons in comparison to a control DNA having the Insertion(s).

"Primer" as used herein refers to an oligonucleotide molecule with a length of 7-40 nucleotides, preferably 10-38 nucleotides, preferably 15-30 nucleotides, or 15-25 nucleotides, or 17-20 nucleotides. For example, the primer can an oligonucleotide having a length of 7, 8, 9, 10, 11, 12, 13, 14, 15, 16, 17, 18, 19, 20, 21, 22, 23, 24, 25, 26, 27, 28, 29 or 30 nucleotides. Primers are usually used in the amplification of a DNA sequence by polymerase chain reaction (PCR) as well known in the art. For a DNA template sequence to be amplified, a pair of primers can be designed at its 5' upstream and its 3' downstream sequence, i.e. 5' primer and 3' primer, each of which can specifically hybridize to a separate strand of the DNA double strand template. 5' primer is complementary to the anti-sense strand of the DNA double strand template; and 3' primer is complementary to the sense strand of the DNA template. As known in the art, the "sense strand" of a double stranded DNA template is the strand which contains the sequence identical to the mRNA sequence transcribed from the DNA template (except that "U" in RNA corresponds to "T" in the DNA) and encoding for a protein product. The complementary sequence of the sense strand is the "anti-sense strand." In the present disclosure, all the SEQ ID NOs are sense strand DNA, and the sequences to which the SEQ ID NOs are complementary are anti-sense strand DNA.

"Hybridize to" as used herein refers to the process of hydrogen bond formation between a primer and a template DNA through base pairing. "Specifically hybridize to" as used herein means that a sufficient number of hydrogen bonds are formed between the primer and the template DNA, so that the template DNA can be amplified by PCR. In certain embodiments, at least 70%, 75%, 80%, 85%, 90%, 95%, 97%, 98%, 99% or 100% nucleotides of the primer form hydrogen bonds with the template DNA. In certain embodiments, the primer is at least 70%, 75%, 80%, 85%, 90%, 95%, 97%, 98%, 99% or 100% complementary to the template DNA. In certain embodiments, the term "specifically hybridize to" refers to a primer having a fragment of oligonucleotides which 100% hybridizes to, or is continuously complementary to its target DNA.

Primers can be used to amplify the DNA template sequence through PCR reaction. PCR usually includes multiple reaction cycles, each of which includes a denaturation step, an annealing step and an extension step, etc. During denaturation, the reaction is heated to a high temperature and the DNA double strand melt into single-stranded DNA molecules. The temperature is lowered to the annealing temperature, at which the 5' primer and 3' primer specifically hybridize to their target sequences respectively on each of the single strands of the DNA template. The DNA template sequence hybridized with the 5' primer is referred to as 5' upstream sequence, and the DNA template sequence hybridized with the 3' primer is referred to as the 3' downstream sequence. During the extension step, the DNA polymerase extends the primers at its 3' end by adding nucleotides that are complementary to the DNA template in 5' to 3' direction, thereby synthesizes a new DNA strand that is complementary to the DNA template strand. The newly synthesized DNA chain can serve as DNA template in subsequent reaction cycles. In this way, the DNA template sequence between the 5' upstream sequence and the 3' downstream sequence (i.e. the sequence to be amplified) can be exponentially amplified through PCR, and the DNA product obtained thereof is usually referred to as an amplicon. Typically, the length of an amplicon is longer than or at least equal to the sum of the lengths of 5' primer and 3' primer. The amplicon has a sense strand whose 5' end sequence is the sequence of the 5' primer, and an anti-sense strand whose 5' end sequence is the sequence of the 3' primer.

The amplicon can be detected or analyzed to indicate the presence or absence of an insertion in a target sequence. For example, the amplicon can be detected for its presence, its size, and/or its sequence and determined to have the Insertion(s) in comparison to a control amplicon having the Insertion(s).

The presence of an amplicon can be detected by any suitable methods known in the art, for example, without limitation, by agarose gel electrophoresis. Suitable detection molecules can be selected for the detection, for example, but without limitation, DNA double strand intercalative dye (such as ethidium bromide, fluorescent stains that bind to DNA double strand, etc.). The size (e.g. molecular weight) of an amplicon can be measured by, for example, agarose gel electrophoresis, optionally with a DNA molecular weight marker. For DNA sequencing, a sequence analyzer can be used to obtain the nucleotide sequence of the amplicon.

Examples of the pairs of isolated oligonucleotide 5' primer and 3' primer are provided in the present disclosure, for which PCR amplification is indicative of the absence or presence of an Insertion (e.g. Insertion I, Insertion II, or Insertion III) in the intron 1 of the FADS2 gene. For example, primers are designed to amplify DNA fragments in a subject in comparison to a control DNA (having the Insertions(s)), and the size of the amplicon of the subject is compared to the size of the control amplicon and indicative of the presence or absence of the Insertion(s) (e.g., if both amplicons have the same size, then the subject DNA has the Insertion(s), if the amplicon of the subject is smaller than the control amplicon, the subject DNA lacks the Insertion(s)). For another example, primers can be designed to only amplify the DNA fragment having the Insertion(s) but not the DNA without the Insertion(s). Alternatively, primers can be designed to only amplify the DNA fragment without the Insertion(s) but not the one with the Insertion(s).

As is known in the art, a suitable primer hybridization position and a primer sequence can be selected according to the common knowledge of a skilled artisan. For example, the position of primer hybridization can be selected according to the length of the sequence to be amplified. For example, if the position of the 5' primer is determined, then the hybridization position of the 3' primer can be selected based on the expected size of amplified product and the hybridization position of 5' primer, and vice versa.

A person skilled in the art can determine a suitable length of the amplified product according to the common knowledge in the art. In certain embodiments, the length of an amplified product is less than or equals to 2000 base pair (2000 bp), 1500 bp, 1000 bp, 500 bp, 400 bp, 300 bp, or 200 bp. In certain embodiments, the length of an amplified product can range from, for example, about 100 bp to about 2000 bp, about 100 bp to about 1500 bp, about 100 bp to about 1000 bp, about 100 bp to about 900 bp, about 100 bp to about 800 bp, about 100 bp to about 700 bp, about 100 bp to about 600 bp, about 100 bp to about 500 bp, about 100 bp to about 400 bp, about 100 bp to about 300 bp, about 100 bp to about 200 bp, etc.

Once the positions for primer hybridization are selected and/or the length and sequence of amplified fragment are determined, the primer sequence and PCR protocols can be readily designed using methods known in the art, see, for example, J. Bartlett et al, PCR Protocols, published by Humana Press, 2003; A. Yuryev, PCR primer design, published by Humana Press, 2007.

In certain embodiments, amplification using the pair of primers provided herein is indicative of absence or presence of Insertion I.

Figure 7A:
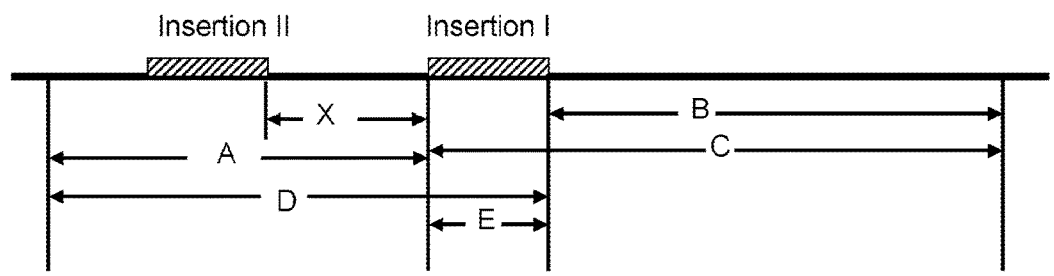
FIG. 7. Schematic drawings showing the regions on intron 1 of the FADS2 gene where primers can be designed to detect presence or absence of Insertion I (FIG. 7A), Insertion II (FIG. 7B), and Insertion III (FIG. 7C).

In certain embodiments, the 5' primer specifically hybridizes to a sequence antisense to Fragment A (see FIG. 7A, SEQ ID NO: 7), Fragment D (see FIG. 7A, SEQ ID NO: 10), Fragment E (see FIG. 7A, SEQ ID NO: 11), or Fragment X (see FIG. 7A, SEQ ID NO: 23); and the 3' primer specifically hybridizes to a sequence of Fragment B (see FIG. 7A, SEQ ID NO: 8).

In certain embodiments, the 5' primer specifically hybridizes to a sequence antisense to Fragment A (see FIG. 7A, SEQ ID NO: 7) or Fragment X (see FIG. 7A, SEQ ID NO: 23); and the 3' primer specifically hybridizes to a sequence of Fragment B (see FIG. 7A, SEQ ID NO: 8), Fragment C (see FIG. 7A, SEQ ID NO: 9) or Fragment E (see FIG. 7A, SEQ ID NO: 11).

Fragment A refers to the sequence that spans from the $1^{st}$ nucleotide to the $317^{th}$ nucleotide of SEQ ID NO: 20. Fragment B refers to the sequence that spans from the $340^{th}$ nucleotide to the $629^{th}$ nucleotide of SEQ ID NO: 20, Fragment C spans from the $318^{th}$ nucleotide to the $629^{th}$ nucleotide of SEQ ID NO: 20, Fragment D spans refers to the sequence that from the $1^{st}$ nucleotide to the $339^{th}$ nucleotide of SEQ ID NO: 20, and Fragment E refers to the sequence that spans from the $318^{th}$ nucleotide to the $339^{th}$ nucleotide of SEQ ID NO: 20. Fragment X refers to the sequence that spans from the $243^{rd}$ nucleotide to the $317^{th}$ nucleotide of SEQ ID NO: 20.

The pair of primers can be designed to be flanking the Insertion I and capable of amplifying the intron 1 of the FADS2 gene or SEQ ID NO: 20. By "flanking," it is meant when both the 3' primer and the 5' primer hybridize to the target DNA double strand, the 3' end of the 5' primer is 5' upstream to the Insertion, and the 3' end of the 3' primer is 3' downstream to the insertion on that DNA double strand, and optionally, the ends of the primers are separated from the insertion by one or more nucleotides. In certain embodiments, the 5' primer may be designed to hybridize to a sequence antisense to Fragment A, and the 3' primer may be designed to hybridize to a sequence of Fragment B. The size of the resulting amplicon is assessed to determine whether the subject DNA has or has not a 22-nucleotide Insertion I (SEQ ID NO. 1) by sequencing or by comparing to a control amplicon having Insertion I.

In certain embodiments, amplification using the pair of primers provided herein is indicative of absence or presence of Insertion II. In certain embodiments, the 5' primer specifically hybridizes to a sequence antisense to Fragment F (see FIG. 7B, SEQ ID NO:12), or Fragment H (see FIG. 7B, SEQ ID NO: 14); and the 3' primer specifically hybridizes to a sequence of Fragment G (see FIG. 7B, SEQ ID NO: 13), or Fragment X (see FIG. 7B, SEQ ID NO: 23).

Figure 7B:
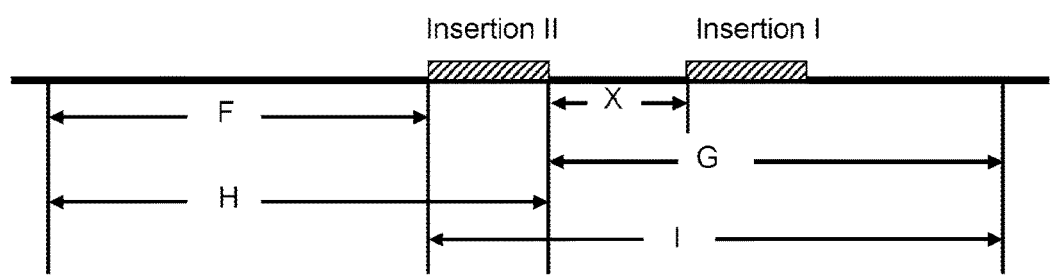

In certain embodiments, the 5' primer specifically hybridizes to a sequence antisense to Fragment F (see FIG. 7B, SEQ ID NO: 12); and the 3' primer specifically hybridizes to a sequence of Fragment G (see FIG. 7B, SEQ ID NO: 13), Fragment I (see FIG. 7B, SEQ ID NO: 15), or Fragment X (see FIG. 7B, SEQ ID NO: 23).

Fragment F refers to the sequence that spans from the $1^{st}$ nucleotide to the $239^{th}$ nucleotide of SEQ ID NO: 20. Fragment G refers to the sequence that spans from the $243^{rd}$ nucleotide to the $629^{th}$ nucleotide of SEQ ID NO: 20, Fragment H refers to the sequence that spans from the $1^{st}$ nucleotide to the $242^{nd}$ nucleotide of SEQ ID NO: 20, and Fragment I refers to the sequence that spans from the $240^{th}$ nucleotide to the $629^{th}$ nucleotide of SEQ ID NO: 20.

The pair of primers can be designed to be flanking the Insertion II and capable of amplifying at least partial of SEQ ID NO: 4, and/or SEQ ID NO: 20. In certain embodiments, the 5' primer may be designed to hybridize to a sequence antisense to Fragment F, and the 3' primer may be designed to hybridize to Fragment G. The resulting amplicons can be sequenced to determine presence of absence of Insertion II.

In certain embodiments, the pair of 3' primer and 5' primer is capable of amplifying at least partial of SEQ ID NO: 5, and/or SEQ ID NO: 21. In such case, the amplicons can be further characterized in terms of nucleotide sequence, so as to determine the presence or absence of Insertion II in the amplicon. If the target sequence contains the Insertion, then the amplicon would have the sequence of Insertion II.

In certain embodiments, the pair of primers can be designed to amplify at least partial of SEQ ID NO: 4 and/or SEQ ID NO: 20 if the subject DNA sequence contains Insertion II but not if the subject DNA sequence lacks Insertion II. In certain embodiments, one primer can be designed to hybridize the sense or antisense of SEQ ID NO. 4 and at least one nucleotide (or two or all three) of the primer is or complements to nucleotides numbers 51 to 53 of SEQ ID NO 4 (or nucleotide numbers 240-242 SEQ ID NO 20). For example, 3' end of the 5' primer is nucleotide numbers 51, 51-52, or 51-53 of SEQ ID NO 4 (or nucleotide numbers 240, 240-241, or 240-242 SEQ ID NO 20). For another example, 3' end of the 3' primer complements to nucleotide numbers 53, 52-53, or 51-53 of SEQ ID NO. 4 (or nucleotide numbers 242, 241-242, or 240-242 SEQ ID NO 20). The presence of an amplicon (in comparison to a control DNA having the Insertion II) indicates the presence of Insertion II in a test subject while the absence of an amplicon indicates otherwise.

In certain embodiments, when the primer is aligned with SEQ ID NO: 5 (or SEQ ID NO: 21) to allow the maximum number of base pairing, at least one nucleotide (e.g. 1, 2, or 3 nucleotides) at the 3' end of the primer is/are mismatched (i.e. do(es) not form Waston-Crick base pair with the corresponding base(s) in SEQ ID NO: 5 or SEQ ID NO: 21). Such mismatch at 3' end of the primer would lead to failure in primer extension in PCR, and hence failure in producing a detectable amplicon. In such case, the presence of an amplicon in a PCR reaction would indicate the presence of Insertion II in the target sequence, and the absence of an amplicon would indicate the absence of Insertion II.

In certain embodiments, the pair of primers can be designed to result in amplicon in a PRC reaction if the subject DNA sequence has no Insertion II but not if the subject DNA sequence contains Insertion II. In certain embodiments, one primer can be designed to hybridize the sense or antisense of SEQ ID NO. 5 and at least two continuous nucleotides of the primer are or complement to nucleotides numbers 50 to 52 of SEQ ID NO 5 (see FIG. 8D). The presence of an amplicon (in comparison to a control DNA having the Insertion II) indicates the absence of Insertion II in a test subject while the absence of an amplicon indicates otherwise.

For example, at least one primer may be designed to span continuously nucleotides 50 and 51 ("CC") and the adjacent sequences in SEQ ID NO: 5, in which nucleotides 50 and 51 of SEQ ID NO: 5 corresponds to nucleotides 50 and 54 of SEQ ID NO: 4, flanking the 3 bp Insertion II (see FIGS. 8C and 8D). In certain embodiments, when the primer is aligned with SEQ ID NO: 4 or SEQ ID NO: 20 to allow the maximum number of base pairing, at least one nucleotide (e.g. 1, 2, or 3 nucleotides) at the 3' end of the primer is/are mismatched (i.e. do(es) not form Watson-Crick base pair with the corresponding base(s) in SEQ ID NO: 4 or SEQ ID NO: 20). Such mismatch at 3' end of the primer would lead to failure in primer extension in PCR, and hence failure in producing a detectable amplicon. In such case, the presence of an amplicon in a PCR reaction would indicate the absence of Insertion II in the target sequence, and the absence of an amplicon would indicate the presence of Insertion II.

In certain embodiments, amplification using the pair of primers provided herein is indicative of absence or presence of Insertion III.

Figure 7C:
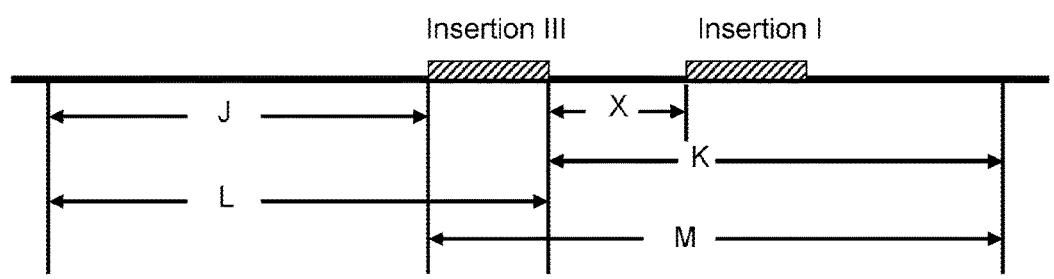

In certain embodiments, the 5' primer specifically hybridizes to a sequence antisense to Fragment J (see FIG. 7C, SEQ ID NO: 16), or Fragment L (see FIG. 7C, SEQ ID NO: 18); and the 3' primer specifically hybridizes to a sequence of Fragment K (see FIG. 7C, SEQ ID NO: 17) or Fragment X (see FIG. 7C, SEQ ID NO: 23).

In certain embodiments, the 5' primer specifically hybridizes to a sequence antisense to Fragment J (see FIG. 7C, SEQ ID NO: 16); and the 3' primer specifically hybridizes to a sequence of Fragment K (see FIG. 7C, SEQ ID NO: 17), Fragment M (see FIG. 7C, SEQ ID NO: 19), or Fragment X (see FIG. 7C, SEQ ID NO: 23).

Fragment J refers to the sequence that spans from the $1^{st}$ nucleotide to the $241^{st}$ nucleotide of SEQ ID NO: 20. Fragment K refers to the sequence that spans from the $243^{rd}$ nucleotide to the $629^{th}$ nucleotide of SEQ ID NO: 20, Fragment L refers to the sequence that spans from the $1^{st}$ nucleotide to the $242^{nd}$ nucleotide of SEQ ID NO: 20, and Fragment M refers to the sequence that spans from the $242^{nd}$ nucleotide to the $629^{th}$ nucleotide of SEQ ID NO: 20.

The pair of primers can be designed to be flanking the Insertion III and capable of amplifying at least partial of SEQ ID NO: 4, and/or SEQ ID NO: 20. In certain embodiments, the 5' primer may be designed to hybridize to a sequence antisense to Fragment J, and the 3' primer may be designed to hybridize to a sequence of Fragment K. The resulting amplicons can be sequenced to determine the presence or absence of "A" (Insertion III) in SEQ ID NO. 4.

In certain embodiments, the pair of 3' primer and 5' primer is capable of amplifying at least partial of SEQ ID NO: 6, and/or SEQ ID NO: 22. In such case, the amplicons can be further characterized in terms of nucleotide sequence, so as to determine the presence or absence of Insertion III in the amplicon. If the target sequence contains the Insertion, then the amplicon would have the sequence of Insertion III.

In certain embodiments, the pair of primers can be designed to result in amplicons if the subject DNA sequence contains Insertion III but not if the subject DNA sequence lacks Insertion III. In certain embodiments, one primer can be designed to hybridize the sense or antisense of SEQ ID NO. 4 and one nucleotide of the primer is or complements to nucleotide numbers 53 of SEQ ID NO 4 (or nucleotide number 242 of SEQ ID NO: 20). For example, 3' end of the 5' primer is nucleotide number 53 of SEQ ID NO: 4 (or nucleotide number 242 of SEQ ID NO: 20). For another example, 3' end of the 3' primer complements to nucleotide number 53 of SEQ ID NO. 4 (or nucleotide number 242 of SEQ ID NO: 20). The presence of an amplicon (in comparison to a control DNA having the Insertion III) indicates the presence of Insertion III in a test subject while the absence of an amplicon indicates otherwise.

In certain embodiments, when the primer is aligned with SEQ ID NO: 6 or SEQ ID NO: 22 to allow the maximum number of base pairing, the nucleotide at the 3' end of the primer is mismatched (i.e. does not form Watson-Crick base pair with the corresponding base in SEQ ID NO: 22). Such mismatch at 3' end of the primer would lead to failure in primer extension in PCR, and hence failure in producing a detectable amplicon. In such case, the presence of an amplicon in a PCR reaction would indicate the presence of Insertion III in the target sequence, and the absence of an amplicon would indicate the absence of Insertion III.

In certain embodiments, the pair of primers can be designed to result in an amplicon in a PCR reaction if the subject DNA sequence has no Insertion III but not if the subject DNA sequence contains Insertion III. In certain embodiments, one primer can be designed to hybridize the sense or antisense of SEQ ID NO. 6 and at least two continuous nucleotides of the primer are or complement to nucleotides numbers 52 to 53 of SEQ ID NO 6 (see FIG. 8E). The presence of an amplicon (in comparison to a control DNA having the Insertion III or a control DNA having no Insertion III) indicates the absence of Insertion III in a test subject while the absence of an amplicon indicates otherwise.

For example, at least one primer may be designed to span continuously nucleotides 52 and 53 ("CC") and the adjacent sequences in SEQ ID NO: 6, in which nucleotides 52 and 53 of SEQ ID NO: 6 corresponds to nucleotides 52 and 54 of SEQ ID NO: 4, flanking the 1 bp Insertion III (see FIGS. 8C and 8E). In certain embodiments, when the primer is aligned with SEQ ID NO: 4 or SEQ ID NO: 20 to allow the maximum number of base pairing, the nucleotide at the 3' end of the primer is mismatched (i.e. does not form Watson-Crick base pair with the corresponding base in SEQ ID NO: 4 or SEQ ID NO: 20). Such mismatch at the primer would lead to failure in primer extension in PCR, and hence failure in producing a detectable amplicon. In such case, the presence of an amplicon in a PCR reaction would indicate the absence of Insertion III in the target sequence, and the absence of an amplicon would indicate the absence of Insertion III.

Primer Extension

In primer extension methods, a primer is designed to hybridize immediately upstream of an insertion, and then DNA polymerase extends the hybridized primer by one nucleotide, which corresponds to the first nucleotide in the insertion. If the first nucleotide in the insertion is different from the first nucleotide after the insertion, then extended product would be different and hence can be distinguished.

Primers suitable for this purpose are provided in the present disclosure. In certain embodiments, 5' primers are provided which has at least 7 continuous nucleotides identical to that of Fragment J and has a 3' end positioned at the $52^{nd}$ nucleotide of SEQ ID NO: 4 (or $241^{st}$ nucleotide of SEQ ID NO: 20). In certain embodiments, 3' primers are provided which has at least 7 continuous nucleotides complementary to that of Fragment K and the 3' end positioned at the $54^{th}$ nucleotide of SEQ ID NO: 4 (or $243^{rd}$ nucleotide of SEQ ID NO: 20. Such primer can be useful for detection of presence of Insertion III and/or Insertion II.

Primer extension can be performed with DNA polymerase and dideoxynucleoitde (ddNTP), which can be added to the 3' end of the primer but prevents further extension as it does not have 3'-hydoxyl. For a target sequence containing the insertion (e.g. insertion I or Insertion III), the ddNTP added to the 3' end of the primer is complementary to the first nucleotide of the insertion (i.e. A); for a target sequence lacking the insertion (e.g. insertion I or Insertion III), the ddNTP added to the 3' end of the primer is complementary to the first nucleotide after the insertion (i.e. C). Such difference in the extended ddNTP can be detected using mass-based methods such as MALDI-TOF Mass spectrometry (see, for example, Soderlund-Strand A., et al. "High-throughput genotyping of oncogenic human papilloma viruses with MALDI-TOF mass spectrometry" Clin Chem. 54 (1): 86-92). Since different ddNTPs have different mass, the molecular weight of the extended primers would depend upon the presence or absence of the insertion, and thereby revealing the extended nucleotide which indicates the presence or absence of the insertion. Alternatively, the difference in the extended ddNTP can be detected using fluorescence-based methods. ddNTPs can be conjugated with different fluorescence labels, and the product after the primer extension can be detected for fluorescent signals, which shall reveal the extended nucleotide and indicate the presence or absence of the insertion.

Probe Hybridization

Another aspect of the present disclosure relates to oligonucleotide probes capable of hybridizing to a first fragment of intron 1 of the FADS2 gene containing an insertion and to a second fragment of intron 1 of the FADS2 gene lacking the insertion, but producing detectably different readout between the two, in which the insertion is Insertion I, Insertion II, or Insertion III.

"Readout" as used herein refers to a signal or a parameter that can be qualified or quantified for detection. Probe hybridization can be detected by various methods, and depending on the detection method, the readout can be Tm value, and fluorescence.

Tm value is the temperature at which half of a DNA double-stranded sequence is dissociated (e.g. in single stranded state). One or more mismatches within a short oligonucleotide probe will decrease the Tm value of the DNA duplex formed thereby. Therefore, if an oligonucleotide probe hybridizes to a target sequence at the insertion region (e.g. Insertion I, Insertion II, or Insertion III), the Tm value would be indicate the presence or absence of the insertion.

In certain embodiments, oligonucleotide probes are provided that hybridize to a fragment of SEQ ID NOs: 1, 2, 3, 4, 5 or 6, in which the fragment encompasses at least partial of the region for Insertion I, Insertion II or Insertion III. In certain embodiments, the difference in Tm value is at least 2° C., at least 3° C., at least 4° C., at least 5° C., at least 6° C., at least 7° C., at least 8° C., at least 9° C., or at least 10° C., between the duplex formed with the probe and a target sequence containing the insertion, and the duplex lacking the insertion.

The probes provided herein may be designed into a molecular beacon, which is a oligonucleotide molecule capable of forming a hairpin structure, in which the loop of the hairpin accommodates a probe region for hybridization with a target sequence, and the stem of the hairpin is conjugated with a fluorophore and a quencher at separate ends, so that they are brought in close proximity when the stem is in double stranded form but are separated when the stem dissociates into a single strand. When the molecular beacon is not hybridized to any sequence, the fluorophore will remain quenched by the quencher. But when the molecular beacon is hybridized to its target sequence, the stem of the hairpin will be dissociated and thus result in separation of the quencher from the fluorophore, which can emit detectable fluorescence.

The probes provided herein may also be designed to have a fluorophore and a quencher conjugated at separate ends of the probe, such that in an intact probe, the fluorophore is quenched by the quencher. Such probe can be used in a TaqMan assay, in which the target sequence suspected of containing the insertion is amplified in the presence of the probe using PCR with Taq DNA polymerase, if the target sequence contains the insertion, the probe will hybridize with the target sequence and consequently get degraded by the Taq DNA polymerase as it extends the DNA chain. The fluorophore and the quencher are separated in the degraded probe, thereby emitting fluorescence indicating presence of the insertion. Alternatively, the probes may also be designed to hybridize to a target sequence lacking the insertion, and emits fluorescence to indicate lack of the insertion in the target sequence.

Other methods and techniques for detection of the insertions are known in the art, see for example, Kwok, P. Y. et al, Curr. Issues Mol. Biol. (2003) 5: 43-60; Mills, R. E. et al, Genome Research, (2006) 16: 1182-1190; Yeung, A. T. et al, BioTechniques, (2005)38:749-758; Rigat, B. et al, Nucleic Acids Research, 20 (6): 1433; Wang, J. et al, BioTechniques, (2005)39:885-893; Zhang, J. et al, Autoimmune Diseases, 2012, Article ID 265823. All are incorporated herein by reference in its entirety.

Kits

Another aspect of the present disclosure relates to kits comprising the primers provided herein or an oligonucleotide probe provided herein. The kit can be a research kit, a diagnostic kit, and a kit for any other suitable purpose. The kit may further comprise addition reagents that are useful for the intended methods, for example, a buffer, a control sample, a DNA marker, and so on. The kit may further provide instructions on how to use the kit to detect the insertion.

Diagnostic Methods

Another aspect of the present disclosure relates to methods of determining the need for an FADS-modulating agent or dietary LCPUFA in a subject. The methods comprise a step of determining the presence or absence of Insertion I, Insertion II, and Insertion III in a subject, in which the absence of the at least one of the Insertions is an indication for the need of the FADS-modulating agent and/or dietary LCPUFA. The presence or absence of the Insertions can be determined using any suitable methods known in the art, including PCR-based methods, methods involving primer extension, and methods involving probe hybridization, as provided herein.

In certain embodiments, when PCR-based methods are used, the method further comprises amplifying a fragment of intron 1 of the FADS2 gene in a sample of the subject with a pair of primers provided herein. The presence or absence of the Insertions can be determined according to the primer design, as discussed above. For example, for primers directed to amplify a fragment of intron 1 of the FADS2 gene containing the insertion but not lacking the insertion, absence of an amplicon is indicative of lacking the insertion, and hence the need of the FADS-modulating agent and/or dietary LCPUFA. Interpretations for other primers provided herein can be done accordingly by people skilled in the art in light of the present disclosure.

In certain embodiments, when PCR-based methods are used, the method further comprises determining the absence or presence of any of the Insertions based on the base sequence or molecular weight of the PCR product. For example, primers are designed to amplifying DNA fragments in a subject in comparison to a control DNA (having the Insertions(s)), if both amplicons have the same size, then the subject DNA has the Insertion(s), and if the amplicon of the subject is smaller than the control amplicon, the subject DNA lacks the Insertion(s). Alternatively, the amplicons can be sequenced to determine presence or absence of the Insertion(s).

In certain embodiments, when methods involving primer extension are used, the method further comprises extending the primer provided herein in the presence of the intron 1 of the FADS2 gene from the subject. Similarly, presence or absence of the Insertions can be interpreted from the detection results according to the primer design, and absence of the Insertions indicates the need of the FADS-modulating agent and/or dietary LCPUFA.

In certain embodiments, when methods involving probe hybridization, the method further comprises hybridizing a probe provided herein with the intron 1 of the FADS2 gene from the subject. Similarly, presence or absence of the Insertions can be interpreted from the detection results according to the primer design, and absence of the Insertions indicates the need of the FADS-modulating agent and/or dietary LCPUFA.

In certain embodiment, the presence of SEQ ID NO. 3 and/or the presence of SEQ ID NO. 5 in a subject indicate the need for FADS-modulating agent and/or dietary LCPUFA. In certain embodiment, the presence of SEQ ID NO. 3 but not SEQ ID NO. 2, and/or the presence of SEQ ID NO. 5 but not SEQ ID NO. 4, or the presence of SEQ ID NO. 6 but not SEQ ID NO: 4 indicate the need for FADS-modulating agent and/or dietary LCPUFA.

Preferred Embodiments of the Invention

The fatty acid desaturase genes (FADS1 and FADS2) code for enzymes required for synthesis of omega-3 and omega-6 long-chain polyunsaturated fatty acids (LCPUFA) important in the central nervous system, inflammatory response, and cardiovascular health. Polymorphisms in these genes are associated with numerous health outcomes, but it is unclear how genetic variation affects enzyme function.

Here, we have taken advantage of dense genotyping conducted for the International HapMap Project to achieve fine mapping of an expression quantitative trait locus (eQTL) in the FADS gene cluster. Because previous studies have focused mostly on European-derived populations, the Japanese in Tokyo (JPT) population was chosen for study here. The JPT population has a different linkage disequilibrium (LD) block structure from Europeans, and Polymorphisms have different D/D allele frequencies, so that results are likely to provide new information complementary to existing studies in Europeans. We evaluated gene expression in lymphoblast cell culture, which controls for environmental and hormonal influences that would otherwise reduce power to detect effects; this approach is ideal for a Japanese population, where exposure to pre-formed DHA from high seafood consumption in the traditional diet would otherwise confound any study of FADS gene expression. Single Polymorphisms and haplotypes were evaluated for association with FADS gene expression, and the region of highest association was searched for putative transcription factor binding sites. Cells were treated with transcription factor agonists to test hypotheses, and a novel eQTL associated with SREBP-1c response was identified. Finally, sequencing of the region flanking the putative SREBP-1c binding site revealed two nearby deletion mutations specific to D/D haplotype carriers.

Lymphoblasts obtained from Japanese participants in the International HapMap Project were evaluated for association of expression microarray results with Polymorphisms in the FADS gene cluster. Six Polymorphisms in the first intron of the FADS2 gene were associated with FADS1 expression. A haplotype containing 10 polymorphisms in FADS2 (rs2727270 to rs2851682) present in 24% of the population was associated with lower expression of FADS1. A highly conserved region coinciding with the most significant Polymorphisms contained predicted binding sites for SREBP and PPARγ. Lymphoblasts homozygous for either the I/I or D/D haplotype were treated with agonists for these transcription factors and expression of FADS1 and FADS2 measured. Simvastatin and the LXR agonist GW3965 both upregulated expression of FADS1 and FADS2; no response was found for PPARγ agonist rosiglitazone. Surprisingly, D/D haplotype homozygotes had 20-40% higher induction of FADS1 and FADS2 after simvastatin or GW3965 treatment. All D/D haplotype carriers had two deletions within 150 bp of the putative sterol response element binding site, and none were found among the carriers of I/I haplotype. Individuals carrying the D/D haplotype may be vulnerable to alterations in diet that reduce LCPUFA intake, and especially responsive to statin or marine oil therapy.

In the present disclosure, single Polymorphisms and a haplotype in FADS2 intron 1 were found to be significantly associated with FADS1 expression, measured by both microarray and independently by qRT-PCR. The FADS2 gene is positioned immediately adjacent at a distance of 11.3 kb to FADS1 in a head-to-head orientation on the long arm of human chromosome 11 (See FIG. 5)[24], so that FADS2 intron 1 is upstream of the transcription start site for FADS1. Thus, the existence of an important regulatory region for FADS1 transcription in intron 1 of the FADS2 gene is quite plausible. It has been shown that CYP1A1 and CYP1A2 genes that are adjacent to each other in head-to-head orientation on human chromosome 15 share common bidirectional regulatory regions[25]. The region most highly associated with FADS1 expression overlapped with a conserved region containing predicted binding sites for PPARγ and SREBP. In follow-up experiments, no difference was observed in response to a PPARγ agonist, rosiglitazone, but homozygotes for a D/D haplotype were significantly more sensitive to expression regulation by SREBP-1c modulation. The enhanced response to SREBP-1c was consistently observed for drugs activating SREBP-1c by two different mechanisms: the statin simvastatin upregulates SREBP-1c levels as part of its pleiotropic effects[26], and the LXR agonist GW3965 stimulates the LXR/RXR heterodimer to activate SREBP-1c[27]. Both genotypes upregulated both FADS1 and FADS2 in response to the drugs, but homozygotes for the D/D haplotype exhibited a significantly greater increase in expression of both genes after drug treatment. D/D haplotype homozygotes had final FADS1 levels equivalent to I/I haplotype homozygotes, and 20% higher FADS2 levels. The D/D haplotype was thus associated with two paradoxical states: lower FADS1 expression in the basal state, and stronger upregulation of FADS1 and FADS2 in response to SREBP-1c. The results suggest that the D/D haplotype is associated with enhanced response to SREBP-1c in a binding site with shared regulatory activity for both FADS1 and FADS2. These findings do not explain the reason for lower FADS1 expression in the basal state, but it is possible that a mutation that enhances SREBP-1c binding may be mutually exclusive to binding of another transcription factor in a shared binding region. Sequencing of the candidate region in FADS2 led to the identification of two deletion mutations present only in the D/D haplotype homozygotes, located 81 and 137 bases downstream of the putative SREBP-1c binding site. Although the close proximity to the SRE is highly suggestive of a causal role, further in vitro experimentation is needed to determine whether these InDel mutations affect SREBP-1c binding and activity.

LCPUFA biosynthesis via FADS-encoded desaturase activity is redundant with direct dietary intake of preformed LCPUFA, specifically 20:4n-6, 20:5n-3 and 22:6n-3. Fish intake is recommended in part for its high content of LCPUFA. The traditional Japanese diet delivers on average more than one gram of LCPUFA daily through regular fish consumption[28]. At these levels, only minimal biosynthesis of LCPUFA from linoleic and linolenic acids is metabolically necessary at any life stage, and any differences in desaturase expression and consequent LCPUFA biosynthetic activity between I/I and D/D haplotypes would be masked and presumably of little health consequence. In contrast, typical North American diets provide, on average, less than 300 mg LCPUFA total and thus biosynthesis may be much more important.

Figure 1:
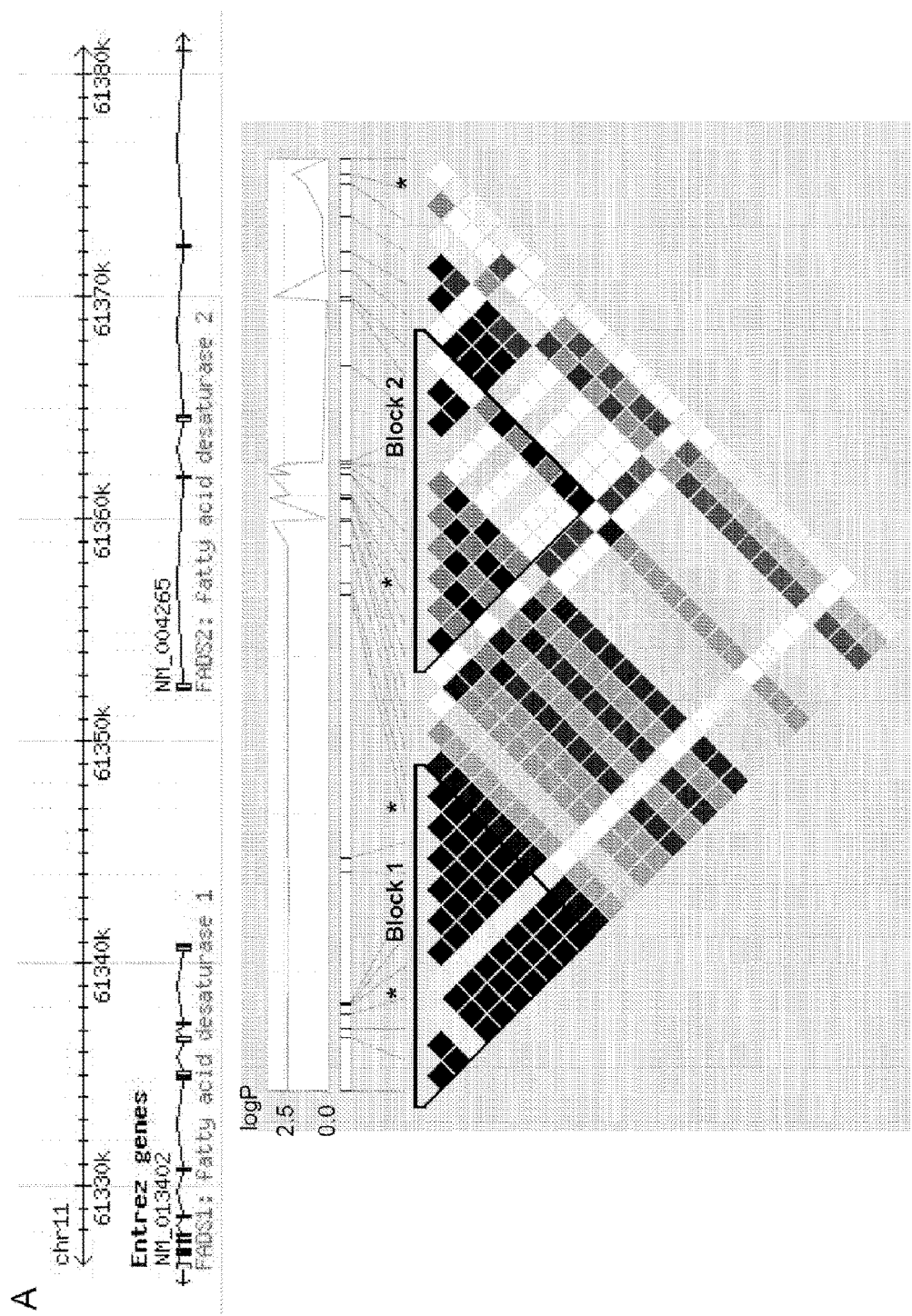
FIG. 1. Expression quantitative trait locus in FADS2 intron 1 and associated haplotype blocks in the Japanese HapMap population. (A) A Manhattan plot of –log(p-value) vs. distance in Kb is shown for the association of individual Polymorphisms with FADS1 expression, with gene annotations above. Two LD blocks for this population are shown, with darkness of shaded cells representing the degree of correlation ($R^2$) between pairs of Polymorphisms. * Marked Polymorphisms were associated with the ratio of arachidonic to linoleic acid (a measure of apparent total desaturase activity) in other Asian populations[11; 35] (B) Haplotypes for each LD block are shown, with I/I alleles for each polymorphism in blue, and D/D alleles in red. Recombination between blocks is depicted by the density of lines connecting individual haplotypes, and the multiallelic D' (0.89).
Figure 1:
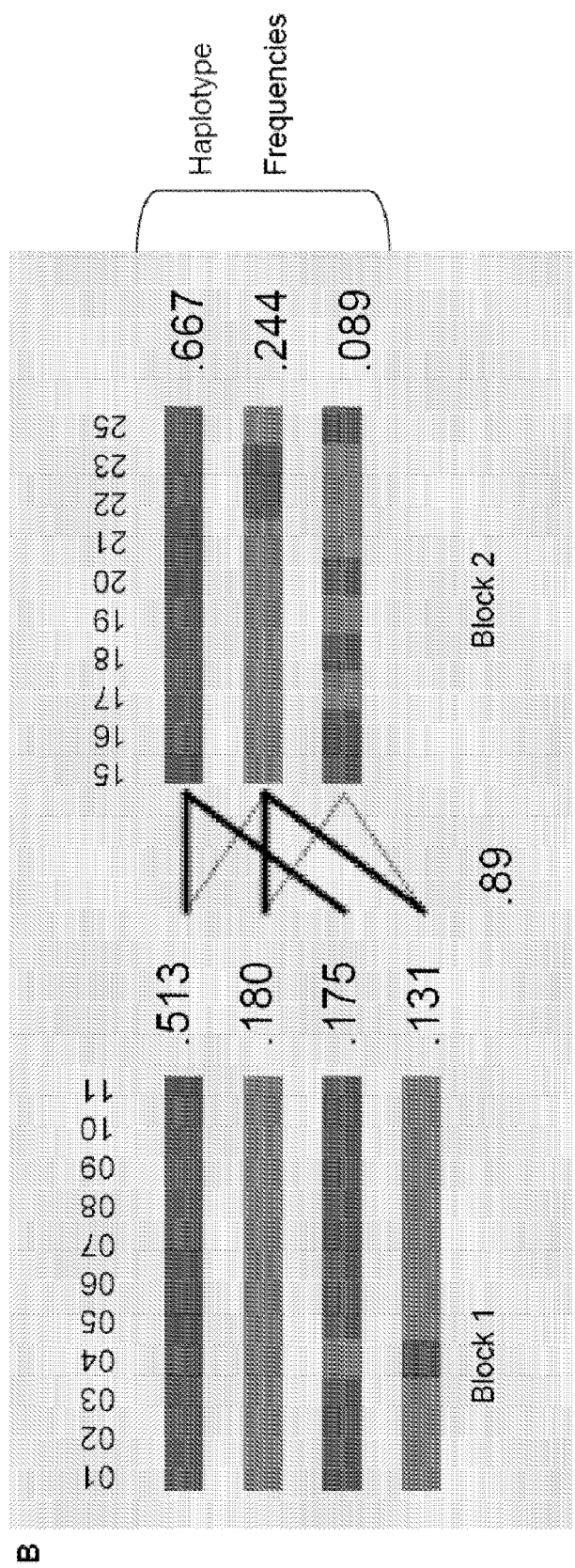

Our in vitro results on human lymphoblasts appear to be relevant to free living humans. Previous studies in Asian populations have linked Polymorphisms in this region with serum fatty acid changes consistent with lower total desaturase activity (noted in FIG. 1), suggesting that the genetic associations observed here can be replicated in human populations. These previous studies suggest that the usual state for individuals carrying these genetic variants is to have basal FADS1 levels so low that they become rate-limiting, reducing overall synthesis of fatty acid end-products. If this is the case, individuals with the D/D haplotype may particularly benefit from diets incorporating higher levels of preformed LCPUFA from fatty fish or marine oil supplements to augment biosynthesis. Thus, although the D/D haplotype is common (present in about one quarter of the Japanese HapMap population), any detrimental effects of the D/D genotype are likely to be masked by the large amounts of fatty fish in the traditional Japanese diet. Importantly, the prevalence of this genetic variant may represent an additional risk to adopting a western diet for many individuals of Japanese descent. Put another way, individuals with the D/D haplotype are predicted to be particularly vulnerable to ill-health when adopting diets that severely reduce preformed LCPUFA intake.

Figure 2:
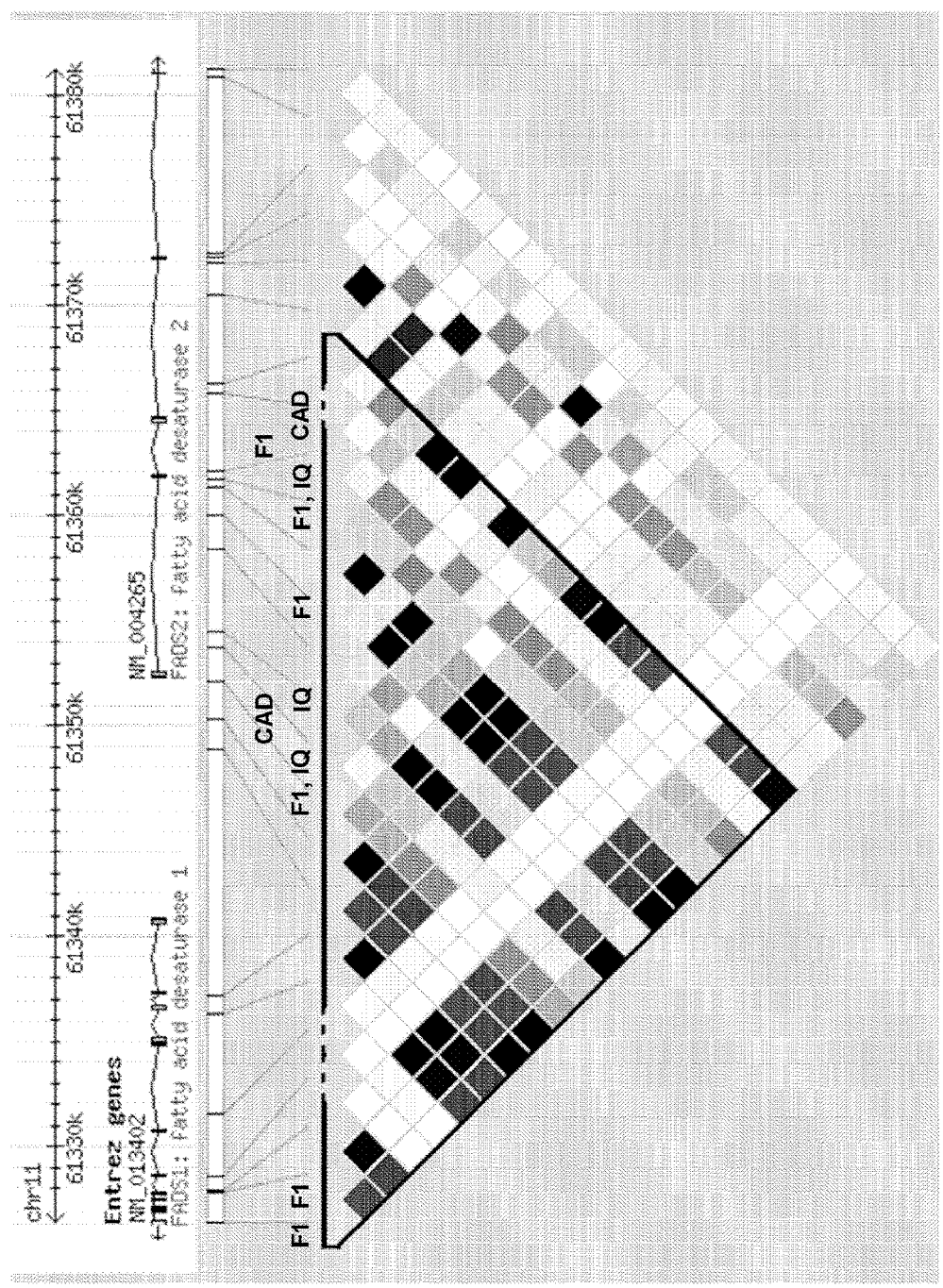
FIG. 2. Haplotype block in European CEU HapMap population. FADS2 intron 1 is contained within a large single LD block in the European HapMap population. Polymorphisms associated with apparent FADS1 activity are in close proximity and in LD with the region highly associated with FADS1 expression in the Japanese population. Abbreviations: F1=Polymorphisms associated with apparent FADS1 activity, inferred from fatty acid product/substrate ratios[11-13]; IQ=Polymorphisms associated with IQ in breast-fed children[9; 36]; CAD=Polymorphisms associated with coronary artery disease and c-reactive protein levels[7].

The data disclosed herein suggest that in populations with low LCPUFA intake, possibly due to low fish consumption, individuals with these genetic variants may have a conditional requirement for LCPUFA. At least some of these populations, such as Americans, derive cardiovascular benefits from statins. A number of previous studies have associated Polymorphisms in FADS2 intron 1 with apparent FADS1 enzyme activity in large studies of European-derived populations (FIG. 2), suggesting that the same causal locus may exist in Europeans as well as Japanese. FIG. 2 also shows that the same region has been associated with IQ in breastfed children, but several studies in various European populations have produced conflicting and sometimes paradoxical results that were not accounted for by differences in fish consumption between populations[6; 9]. However, these studies did not take into account cholesterol, an activator of SREBP-1c[27] present in breastmilk but not in infant formula; population differences in maternal dietary fatty acids and phytosterols may affect breastmilk and infant plasma cholesterol and phytosterol levels[29-31]. In addition, individuals with the D/D haplotype might have lower FADS1 expression in the absence of SREBP-1c activators (such as with infant formula, which does not contain cholesterol), but higher total FADS gene expression in the presence of cholesterol (breastmilk); a similar trend of significantly lower IQ in formula-fed, and almost-significant higher IQ in breastfed children, was observed in one IQ study for several Polymorphisms in FADS2 intron 1[9].

Polymorphisms nearby and in LD with the Polymorphisms most strongly associated with FADS1 expression here have also been associated with coronary artery disease in European studies (FIG. 2). Thus, the finding of enhanced responsiveness to simvastatin for the D/D haplotype may be of special interest. Statins have long been known to increase LCPUFA levels, and there is some previous evidence of changes in apparent desaturase activity in response to statin treatment[32; 33]. Although statins primarily are known for lowering cholesterol by inhibiting HMG-CoA reductase, they also have numerous pleiotropic effects that contribute to their medical benefits, including improved endothelial function and reduced inflammation and thrombosis. It has been theorized that statins' pleiotropic effects may be primarily due to alterations in LCPUFA levels[33]. Interestingly, diets high in omega-3 LCPUFA were found to reduce overall and cardiac mortality by the same amount as statin treatment[34]. Here, we show that simvastatin upregulates both FADS1 and FADS2. The D/D haplotype identified here was associated with an especially strong response to simvastatin. Assuming living humans have similar responses as observed in lymphoblasts, individuals with the D/D haplotype may have lower basal FADS1 expression, leading to lower LCPUFA production. Fortunately, simvastatin is shown here to correct the basal deficiency in FADS1 expression, and to produce FADS2 expression that would be higher than in other statin users; our results predict that D/D haplotype carriers would have especially high LCPUFA synthesis after simvastatin treatment, and thus would especially benefit from pleiotropic effects attributed to LCPUFA production.

Our results highlight an extreme example of gene-environment interaction, in which a D/D haplotype is associated with either lower, or higher, desaturase expression depending on levels of SREBP-1c or LXR agonists. Environmental factors can be adjusted to mitigate potential harm for D/D haplotype carriers: diet can easily be modified to enhance SREBP-1c or LXR activity via natural ligands, or to take in pre-formed LCPUFA and minimize the need for biosynthesis. Moreover, carriers of this D/D haplotype who are candidates for statin treatment may especially benefit from these drugs, as well as possibly from future LXR agonist drugs currently under development.

EXAMPLES

Example 1. Materials and Methods a) Single Polymorphism Association Analysis

Polymorphism associations were carried out for Polymorphisms in the FADS gene cluster using publicly available data from 46 International HapMap lymphoblast cell lines for the Japanese in Tokyo (JPT) population. Normalized expression data from the Illumina Sentrix Human-6 Expression BeadChip Microarray were obtained from the Gene Expression Omnibus (Series GSE6536)[16; 17]. Genotype information for lymphoblast cell lines was obtained from the Coriell Institute for Medical Research polymorphism Browser. All genotyped Polymorphisms were used, excluding those non-polymorphic in the JPT population. Single polymorphism associations and multiple test correction were carried out in PLINK v1.07[18] using linear regression, with a dominant model chosen because of lack of power in this small sample size to detect additive effects. Individuals or Polymorphisms missing more than 30% of genotypes were excluded, as well as Polymorphisms with D/D allele frequency below 1%, or p-value<0.001 for deviation from expected frequency of genotypes in the population (Hardy-Weinberg equilibrium).

b) Haplotype Association Analysis

Phase was imputed and haplotypes identified in the Japanese and European (CEU) HapMap populations using Haploview v4.2[19]. Linkage disequilibrium blocks were defined by the confidence interval-based algorithm of Gabriel et al.[20]. Identical parameters were used to calculate blocks in both populations. Haplotype associations were carried out in PLINK v1.07 by linear regression with an additive model, using the max(T) permutation procedure with 10,000 permutations to correct for multiple testing. Exclusion criteria were the same as for individual polymorphism associations, except that Polymorphisms or individuals missing more than 10% of genotypes were excluded. Haplotype allele frequencies lower than 5% were also excluded from analysis.

c) Conserved Regions and Transcription Factor Binding Predictions

Genomic sequence alignment calculating percent identity of multiple species compared with the human sequence was carried out with mVISTA[21]. Predicted transcription factor binding sites were identified by TRANSFAC Professional 9.2 database search combined with comparative sequence analysis, using rVISTA (regulatory VISTA)[22].

d) Lymphoblast Cell Culture, Treatments, and RNA Extraction

Immortalized B-lymphocyte (lymphoblast) cell lines from Japanese HapMap participants were obtained from the Coriell Institute for Medical Research, and used within 10 passages of receipt from the repository. Cells were grown in RPMI 1640 with 2 mM L-alanyl-glutamine (Sigma) and 15% fetal bovine serum (media and serum obtained from HyClone) in a humidified environment at 37° C. with 5% $CO_2$. All experiments were conducted on cells grown and treated in parallel in identical media and growth conditions. Cells were treated with 5 µNl simvastatin (Sigma), 1 µNl GW3965 (Sigma), or 20 µM rosiglitazone (Cayman Chemicals), or vehicle for 24 hours before collecting lysates. RNA was extracted using the RNeasy kit (Qiagen), and RNA quality was checked by agarose gel electrophoresis to verify RNA integrity and by 260/280 nm ratios on a NanoDrop 2000 (Thermo Scientific). cDNA was prepared using the High Capacity cDNA Reverse Transcription Kit (Applied Biosystems) according to the manufacturer's protocol.

e) Quantitative Real-Time PCR

Quantitative real-time PCR was carried out using SYBR Green Master Mix (Roche) on a LightCycler 480 instrument (Roche). PCR primers were obtained from Integrated DNA Technologies (sequences available upon request), except for 18S, which was obtained from Qiagen as a QuantiTect Primer Assay. PCR reaction efficiency was calculated from standard curves, and reactions were assessed by both melting curves and by running on agarose gels to verify reaction products and the absence of primer-dimers. Quantitative cycle (Cq) values were determined using LightCycler 480 SW1.5.0SP3 software, version 1.5.0.39 (Roche). Relative quantification was carried out using the Pfaffl method[23], taking into account reaction efficiency and using multiple reference genes for greater accuracy (β-actin, GAPDH, and 18S). Before proceeding with analysis, basal expression was shown to be invariant by vehicle-only treatment for all genes studied. Statistical significance of differences in fold changes between genotypes in response to cell treatments (normalized to vehicle treatment for each genotype) was assessed by the Mann-Whitney U test. Bootstrapping and randomization techniques were used in REST 2009 software (Qiagen) to calculate significance of fold changes normalizing both genotypes to basal expression in I/I allele homozygotes.

f) Sequencing of Candidate Sterol Response Element Regions

A total of about 5 million cells from lymphoblast cultures were harvested for DNA extraction. DNA extraction was performed using DNeasy Blood & Tissue Kit (Qiagen). A 629 base pair portion (bases 6908015-6908643; GenBank Accession Number NT_167190.1) of FADS2 intron 1 and a 291 base pair portion of FADS1 intron 5 (bases 6882783-6882505; GenBank Accession Number NT_167190.1) flanking the sterol regulatory element (SRE) DNA sequence were amplified using the following primer pairs: FADS2 forward primer 5' TTTCTCAAAGGCCGTGGTGT 3', FADS2 reverse primer 5' AGTGCTAACCACTCCTGGAA 3' and FADS1 forward primer 5' ACAGAGAAT GAAGGGACGCA 3', FADS1 reverse primer 5' ACCCGAAGGAGGCCATATCT 3'. The PCR reactions were carried out using GeneAmp High Fidelity PCR System (Invitrogen). Thermal cycling conditions were: initial denaturation at 94° C. for 5 min followed by 35 cycles of denaturation at 94° C. for 30 s, annealing at 60° C. for 45 s and extension at 72° C. for 1 min, with a final extension at 72° C. for 5 min. PCR products were separated on 2% agarose gels, and the DNA bands were gel eluted and purified using PureLink Quick Gel Extraction Kit (Invitrogen, USA). The purified products were sequenced at the Cornell University Life Sciences Core Laboratories Center.

Example 2. Identification of eQTL Associated with FADS1 Expression

Lymphoblast cell cultures derived from all 46 Japanese participants in the International HapMap Project were used to search for genetic variants associated with FADS gene expression. Archived Illumina expression microarray data was obtained from the Gene Expression Omnibus database repository[16; 17]. Analysis was carried out on 41 Polymorphisms densely covering the FADS gene cluster. The Manhattan plot shown in FIG. 1A demonstrated a highly significant region located in FADS2 intron 1 that was associated with lower FADS1 expression for the D/D allele. Within this region, six Polymorphisms passed Bonferroni correction for multiple testing, as shown in Table 1. There were a few nominally significant Polymorphisms associated with FADS2 or FADS3 expression, but none of these passed correction for multiple testing (not shown). Analysis of the linkage disequilibrium (LD) block structure for the Japanese HapMap population revealed two LD blocks in the region of interest, with the most highly significant Polymorphisms primarily in the second block. Three haplotype alleles were observed within Block 2, as shown in FIG. 1B. Polymorphisms in this block were: rs2727270, rs2727271, rs174576, rs2524299, rs174577, rs2072114, rs174578, rs174579, rs174585, and rs2851682. The D/D haplotype present in about one quarter of the population was significantly associated with lower FADS1 expression, as summarized in Table 2.

To estimate relevance of these results to studies in other populations, the LD block structure of the European (CEU) HapMap population is visualized in FIG. 2. Previous large-scale studies, with associated Polymorphisms marked in FIG. 2, found a variety of outcomes associated with the first intron of the FADS2 gene in European-derived populations. In particular, fatty acid changes suggestive of lower FADS1 enzyme activity were found for Polymorphisms in close proximity and in LD with the most highly significant region in the Japanese population.

Example 3. Predicted Transcription Factor Binding Sites

Figure 3:
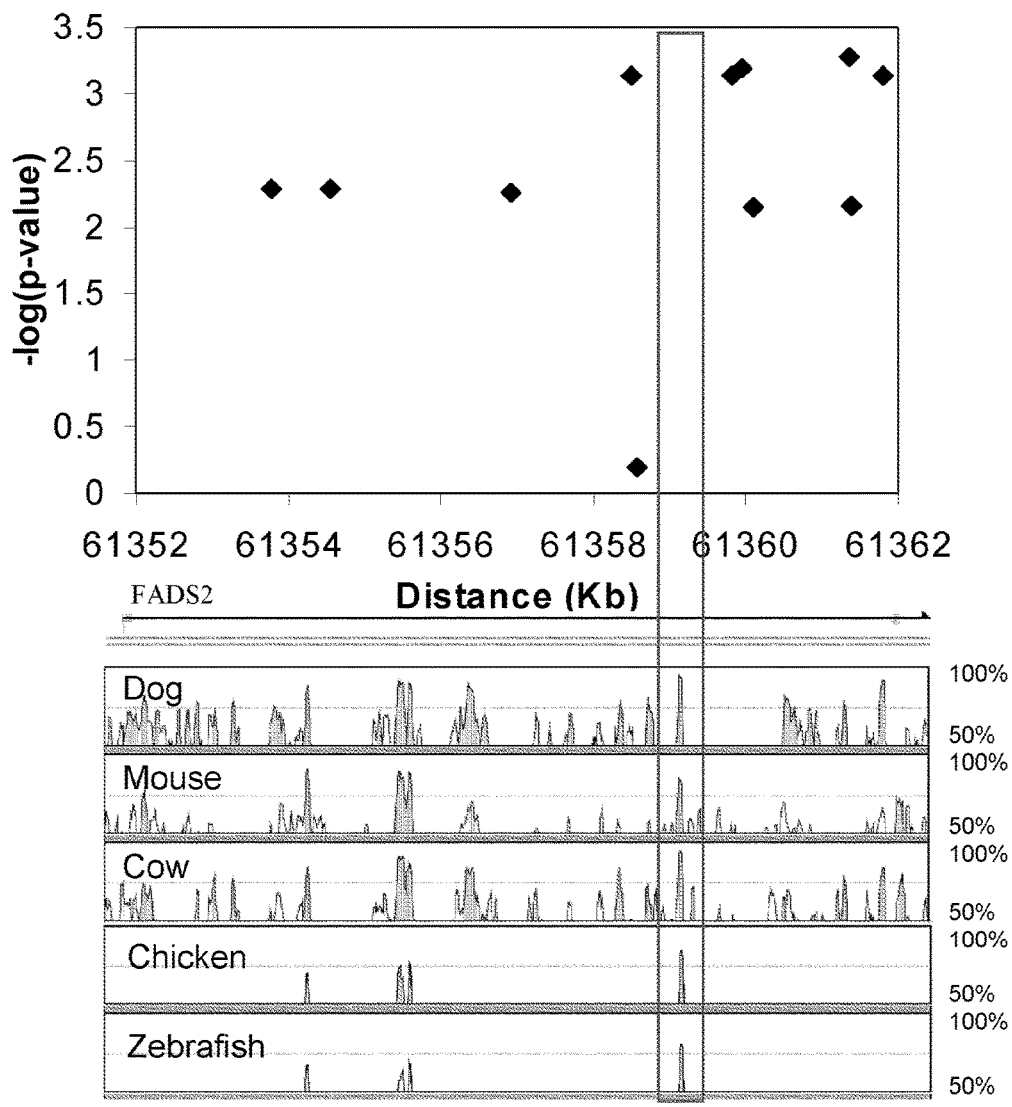
FIG. 3. Conserved region overlapping with significant Polymorphisms in FADS2 intron 1. Zoomed-in detail of FADS2 intron 1 in the Manhattan plot of –log(p-value) vs. base position depicts association of Polymorphisms in the Japanese HapMap population with FADS1 expression, with conserved regions depicted below as percent identity with the human sequence. The red box outlines a region overlapping with the area of highest significance that is conserved from zebrafish to humans, and contains predicted binding sites for SREBP and PPARγ.

To investigate possible causal mechanisms for the lower FADS1 expression associated with this D/D haplotype, the area immediately surrounding the most strongly associated region, and thus most likely to contain the actual causal locus, was examined for predicted regulatory elements. A region highly conserved from zebrafish to humans was identified that overlapped the area containing the most highly significant associated Polymorphisms, as shown in FIG. 3. TRANSFAC database search using the bioinformatics tool rVISTA revealed predicted consensus binding sites in the conserved region for two transcription factors: peroxisome proliferator-activated receptor gamma (PPARγ) and sterol response element binding protein (SREBP). We hypothesized that the significant Polymorphisms identified above could be associated with a genetic variant within one of these binding sites, resulting in altered binding of a transcription factor responsible for regulating FADS1 expression.

Example 4. Lymphoblast FADS1 and FADS2 Expression and Transcription Factor Agonists Follow-up experiments were carried out in Japanese HapMap lymphoblast cell lines homozygous for the D/D haplotype associated with FADS1 expression, or homozygous for the I/I haplotype. All available D/D haplotype homozygote cell lines were used (n=5), as well as randomly chosen I/I allele homozygote cell lines (n=11). FADS1 expression was examined by quantitative real-time PCR, confirming the initial microarray results showing lower FADS1 expression for D/D haplotype homozygotes (FIG. 4A).

Figure 4:
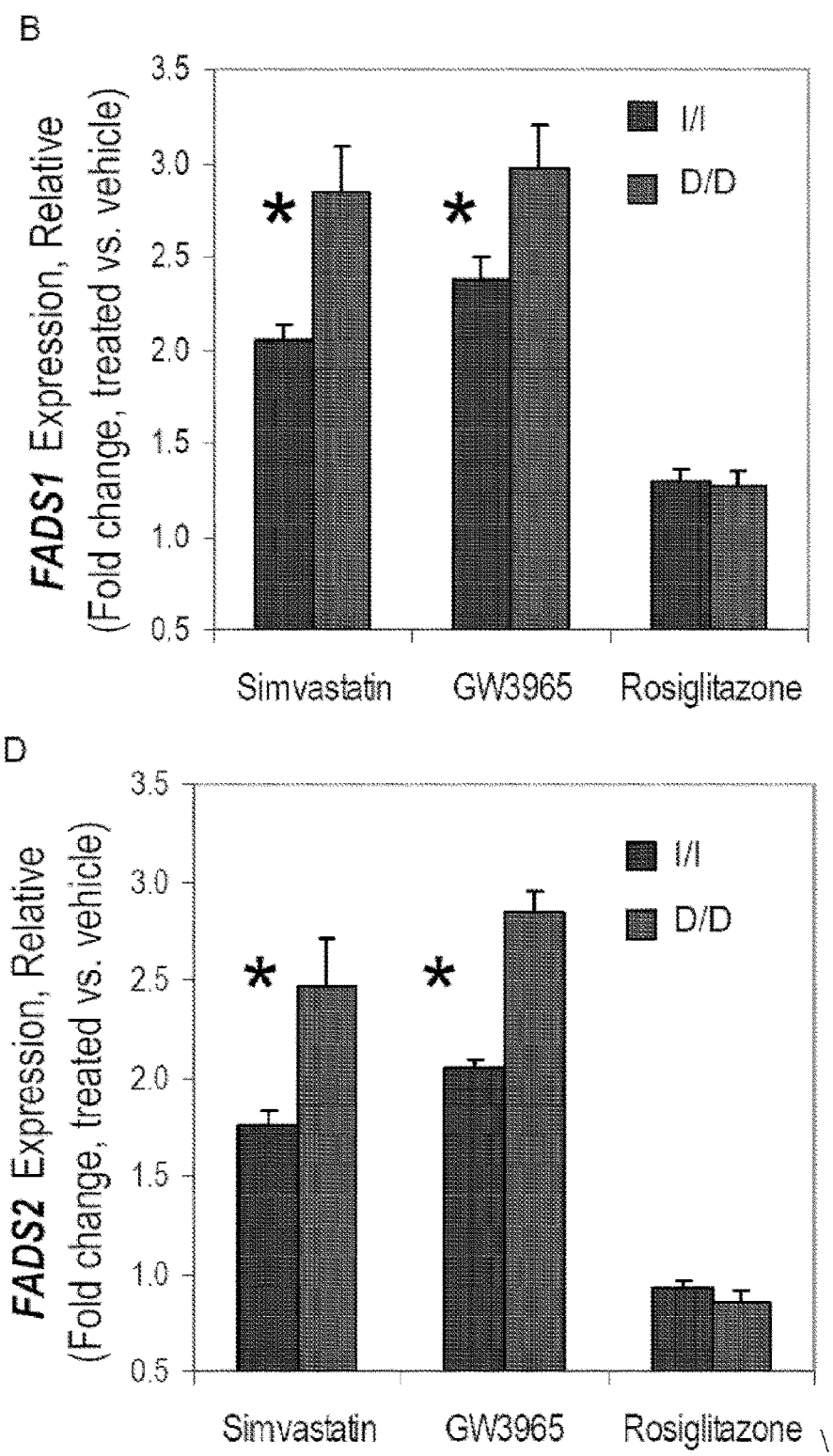
FIG. 4. Basal FADS1 and FADS2 expression and drug response in lymphoblasts homozygous for VI or D/D haplotypes. (A) FADS1 expression normalized to the I/I haplotype cells grown under basal conditions (ordinary growth media=1). Under basal conditions, the D/D haplotype homozygotes had significantly lower basal FADS1 expression than the I/I haplotype homozygotes, and this pattern persisted with rosiglitazone treatment. In contrast, simvastatin or GW3965 treatment upregulated expression in both genotypes such that they were no longer significantly different. (B) The same data as in (A) expressed as the change in FADS1 expression relative to drug treatment, normalized to vehicle treatment (not shown) for each genotype. D/D haplotype homozygotes confirm the findings in (A), showing significantly greater fold increase in FADS1 in response to simvastatin and GW3965 and no difference from I/I haplotype homozygotes in response to rosiglitazone. (C) FADS2 expression normalized to basal condition for the I/I haplotype is equivalent for the two haplotypes under basal conditions and for rosiglitazone. Simvastatin and GW3965 differentially upregulate haplotype FADS2 expression so that the D/D haplotype is greater than the I/I haplotype. (D) The change in FADS2 expression relative to each genotype's vehicle control is significant for simvastatin and GW3965. *p<0.05.

To investigate the possibility of a causal genetic variation in a transcription factor binding site, cells were treated with drugs acting directly or indirectly on PPARγ or SREBP-1c. The PPARγ agonist rosiglitazone produced identical modest FADS1 upregulation responses in I/I and D/D allele homozygotes, so the basal difference in FADS1 expression was maintained even after rosiglitazone treatment, as shown in FIG. 4. Next, two drugs of different classes that alter SREBP-1c by distinct mechanisms were examined: the statin drug simvastatin, and the LXR agonist GW3965. Both treatments upregulated FADS1 by about two-fold in I/I haplotype homozygotes. Unexpectedly, D/D haplotype homozygotes responded even more strongly to modulators of SREBP-1c; upregulation of FADS1 was 40% higher in response to simvastatin, and 25% higher in response to GW3965 for the D/D haplotype (FIG. 4B). These strong responses to SREBP-1c eliminated the difference in FADS1 expression observed in untreated cells, so that the two genotypes did not significantly differ in final FADS1 expression after treatment with simvastatin or GW3965 (FIG. 4A).

Although no difference in basal FADS2 expression for each genotype was observed in the archived microarray data (not shown), both PPARγ and SREBP-1c have previously been implicated as regulators of FADS2 expression. Thus, FADS2 expression with and without the same drug treatments was evaluated. As shown in FIG. 4C, the qRT-PCR results confirmed the microarray results for basal FADS2, with no difference between genotypes, and neither genotype showed any response to rosiglitazone treatment. As with FADS1, SREBP-1c modulators produced about a two-fold increase in FADS2 levels for I/I haplotype homozygotes, and D/D haplotype homozygotes increased FADS2 expression even more in response to simvastatin or GW3965 (FIG. 4D). Because there was no difference in basal FADS2 levels by genotype, final levels of FADS2 were at least 20% higher after statin or LXR agonist treatment in D/D haplotype homozygotes compared to the I/I haplotype group (FIG. 4C). The pattern of response for FADS1 and FADS2 is remarkably consistent (FIGS. 4B and 4D) and the differences in the pattern of total expression (FIGS. 4A and 4C) are due to differences in basal expression.

Example 5. Sequence Differences Near the Putative SREBP-1c Binding Site in FADS2 Intron 1

Based on the difference in response to SREBP-1c, we hypothesized that a sequence variation between the I/I and D/D haplotypes might exist within or in close proximity to a putative sterol response element (SRE) binding site for SREBP-1c. Analysis of FADS1 and FADS2 genes with the rVISTA program revealed two decamer SREs, one in FADS2 intron 1 (5'-ATCACCCCAC-3'), and another in FADS1 intron 5 (5'-ATCACGCCAC-3'). The sequencing of a 291 base pair (bp) fragment flanking the SRE DNA sequence of FADS1 showed no differences between the I/I and D/D haplotypes. However, sequencing of a 629 bp fragment flanking the SRE DNA sequence of FADS2 showed two insertion/deletion (InDel) variants exclusively in the D/D haplotype. As shown in Table 3, a 22 bp (ACTTCTCCCTGCCTCCCCAGGG, SEQ ID NO.1) deletion (rs66698963) was identified by sequencing in all five D/D haplotype homozygotes within a variable number tandem repeat minisatellite sequence located 137 bases downstream of the putative SRE. In addition, a 3 bp deletion (-CCA, rs138766446) located 81 bases downstream of the putative SRE was observed in all but one of the D/D haplotype homozygotes, with the remaining one individual missing only one of the 3 bp (-A, rs149597144). Interestingly, the individual with the -A deletion instead of -CCA consistently had the highest basal FADS1 expression of all of the D/D haplotype homozygotes (data not shown). None of these deletions were observed in any of the eleven I/I haplotype homozygotes.

The ID# rs66698963 within the dbSNP NCBI database is an insertion/deletion genetic variant. In our screening all the I/I haplotype homozygotes showed the presence of both alleles (+/+) and all the D/D haplotype homozygotes showed loss of 22 base pair fragment (ACTTCTCCCTGCCTC-CCCAGGG, SEQ ID NO. 1) in both alleles (-/-; missing is represented as -). We show 50 base pairs flanking either side of the 22 base pair fragment deletion.

rs66698963 (+/+): SEQ ID NO. 2
...CCAGGGCCTCCTCCCTGCCTCCCCAGGGACTTCTCCCTGCCTCCCC

*AGGG*ACTTCTCCCTGCCTCCCCAGG*GCCCT*GGAATAGCACGTCTCTTTT

CCCTGAAAATACTCTTGACCTGATCCT...

rs66698963 (-/-): SEQ ID NO. 3
...CCAGGGCCTCCTCCCTGCCTCCCCAGGGACTTCTCCCTGCCTCCCC

*AGGGCCCT*GGAATAGCACGTCTCTTTTCCCTGAAAATACTCTTGACCTG

ATCCT...

The ID# rs138766446 within the dbSNP NCBI database is an insertion/deletion genetic variant. In our screening all the I/I haplotype homozygotes showed the presence of both alleles (+/+) and 4 out of 5 of the D/D haplotype homozygotes showed loss of 3 base pair fragment in both alleles (-/-; missing is represented as -). The 50 base pair sequences flanking either side of the 3 base pair fragment deletion are shown.

rs138766446 (+/+): SEQ ID NO. 4
CCCTGGGCTCCTCCCTGCCCGCACCCTGGGCCTCCTCCCTGCCTGC*CCCC*

*CCACCCC*AGCCCTCCTCCCTGCCTGCCCCAGGGCCTCCTCCCTGCCTCC

CCA rs138766446 (-/-): SEQ ID NO. 5
CCCTGGGCTCCTCCCTGCCCGCACCCTGGGCCTCCTCCCTGCCTGC*CCCC*

*CCCC*AGCCCTCCTCCCTGCCTGCCCCAGGGCCTCCTCCCTGCCTCCCCA

The ID# rs149597144 within the dbSNP NCBI database is an insertion/deletion genetic variant. In our screening all the I/I haplotype homozygotes showed the presence of both alleles (+/+; yellow font color) and 1 out of 5 of the D/D haplotype homozygotes showed loss of 1 base pair fragment in both alleles (-/-; missing yellow font color and is represented as -). The 50 base pair sequences flanking either side of the 1 base pair fragment deletion are shown.

rs149597144 (+/+): SEQ ID NO. 4
CCCTGGGCTCCTCCCTGCCCGCACCCTGGGCCTCCTCCCTGCCTGCCC

*CCCCACCCC*AGCCCTCCTCCCTGCCTGCCCCAGGGCCTCCTCCCTGC

CTCCCCA rs149597144 (-/-): SEQ ID NO. 6
CCCTGGGCTCCTCCCTGCCCGCACCCTGGGCCTCCTCCCTGCCTGCCC

*CCCCCCCC*AGCCCTCCTCCCTGCCTGCCCCAGGGCCTCCTCCCTGCC

TCCCCA

Example 6

Fatty acid desaturases are enzymes that catalyze the introduction of cis double bonds at specific positions in a fatty acid chain. FADS1, FADS2 and FADS3 are thought to be the key desaturase enzymes involved in the long chain polyunsaturated fatty acid (LCPUFA) biosynthesis. In humans, the three genes (FADS1, FADS2, and FADS3) are clustered within the 100 kb region on long arm of human chromosome 11q12-13.1 and have the same exon/intron organization with 12 exons and 11 introns, similar organization has been seen on mouse chromosome 19[37-38]. Results from our recent studies show extensive splicing of all three desaturases and a novel function of an alternatively spliced isoform[39-41]. In addition, we have identified a 22 bp insertion/deletion (INDEL) genetic variant within intron 1 of FADS2 gene to be associated with either lower, or higher, desaturase expression depending on levels of SREBP-1c or LXR agonists. Individuals homozygous for 22 bp deletion (D/D) showed stronger upregulation of both FADS1 and FADS2 in response to the cholesterol lowering drug simvastatin and the LXR agonist GW3965[42]. This study has been conducted with 16 individual samples from Japanese Hap Map project[42]. In the public dbSNP database the rs66698963 genotype data exist for a single human individual. The genotype of this individual is D/D. The general human population allele frequency is not known for FADS2 INDEL (dbSNP#rs66698963). To investigate the allele frequency of the 22 bp INDEL in general population within US we have isolated DNA from 100 opportunistic human breast milk and placental samples.

Figure 6:
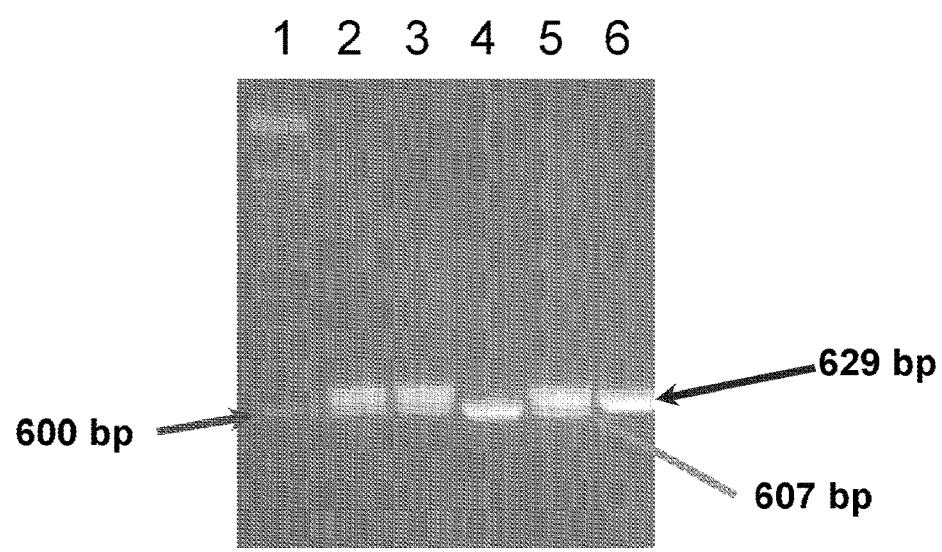
FIG. 6. Agarose gel image of PCR products from 5 individual DNA samples. Three possible genotypes identified for the 22 bp INDEL (deletion/deletion (D/D); insertion/deletion (I/D); insertion/insertion (I/I)) are shown.

A 629 base pair fragment within intron 1 genomic region of FADS2 (GenBank Accession# NT_167190.1) flanking the sterol response element (SRE) was amplified by PCR and tested by 2% agarose gel electrophoresis using 100 human DNA samples. We have identified three genotypes (deletion/deletion (D/D); insertion/deletion (I/D); insertion/insertion (I/I) for the 22 bp INDEL (FIG. 6). Our data shows D/D alleles in 38%, I/D alleles in 40% and I/I alleles in 22%. This pilot study with n=100 sampling size shows the allele frequency of this INDEL in general population in the US. Comparing the Japanese n=16 results to the present results we find that the more abundant allele in the Japanese sample is I, whereas it is D for the n=100 Americans. The American data show that 38% of the individuals carrying D/D genotype are expected to benefit from statin therapy, as well as possibly from future LXR agonist drugs currently under development.

REFERENCES

1. Schmitz, G., and Ecker, J. (2008). The opposing effects of n-3 and n-6 fatty acids. Prog Lipid Res. 47, 147-155.
2. Brenna, J. T., and Diau, G. Y. (2007). The influence of dietary docosahexaenoic acid and arachidonic acid on central nervous system polyunsaturated fatty acid composition. Prostaglandins Leukot Essent Fatty Acids. 77, 247-250.
3. Calder, P. C. (2009). Polyunsaturated fatty acids and inflammatory processes: New twists in an old tale. Biochimie. 91, 791-795.
4. Brookes, K. J., Chen, W., Xu, X., Taylor, E., and Asherson, P. (2006). Association of fatty acid desaturase genes with attention-deficit/hyperactivity disorder. Biol Psychiatry. 60, 1053-1061.
5. Schaeffer, L., Gohlke, H., Muller, M., Heid, I. M., Palmer, L. J., Kompauer, I., Demmelmair, H., Illig, T., Koletzko, B., and Heinrich, J. (2006). Common genetic variants of the FADS1 FADS2 gene cluster and their reconstructed haplotypes are associated with the fatty acid composition in phospholipids. Hum Mol Genet. 15, 1745-1756.
6. Caspi, A., Williams, B., Kim-Cohen, J., Craig, I. W., Milne, B. J., Poulton, R., Schalkwyk, L. C., Taylor, A., Werts, H., and Moffitt, T. E. (2007). Moderation of breastfeeding effects on the IQ by genetic variation in fatty acid metabolism. Proc Natl Acad Sci USA. 104, 18860-18865.
7. Martinelli, N., Girelli, D., Malerba, G., Guarini, P., Illig, T., Trabetti, E., Sandri, M., Friso, S., Pizzolo, F., Schaeffer, L., et al. (2008). FADS genotypes and desaturase activity estimated by the ratio of arachidonic acid to linoleic acid are associated with inflammation and coronary artery disease. Am J Clin Nutr. 88, 941-949.
8. Aulchenko, Y. S., Ripatti, S., Lindqvist, I., Boomsma, D., Heid, I. M., Pramstaller, P. P., Penninx, B. W., Janssens, A. C., Wilson, J. F., Spector, T., et al. (2009). Loci influencing lipid levels and coronary heart disease risk in 16 European population cohorts. Nat Genet. 41, 47-55.
9. Steer, C. D., Davey Smith, G., Emmett, P. M., Hibbeln, J. R., and Golding, J. (2010). FADS2 polymorphisms modify the effect of breastfeeding on child IQ. PLoS One. 5, e11570.
10. Lanka, E., Eggers, S., Moeller, G., Heim, K., Weber, M., Mehta, D., Prokisch, H., Illig, T., and Adamski, J. (2010). A common FADS2 promoter polymorphism increases promoter activity and facilitates binding of transcription factor ELK1. J Lipid Res. 51, 182-191.
11. Merino, D. M., Johnston, H., Clarke, S., Roke, K., Nielsen, D., Badawi, A., El-Sohemy, A., Ma, D. W., and Mutch, D. M. (2011). Polymorphisms in FADS1 and FADS2 alter desaturase activity in young Caucasian and Asian adults. Mol Genet Metab. 103, 171-178.
12. Bokor, S., Dumont, J., Spinneker, A., Gonzalez-Gross, M., Nova, E., Widhaim, K., Moschonis, G., Stehle, P., Amouyel, P., De Henauw, S., et al. (2010). Single nucleotide polymorphisms in the FADS gene cluster are associated with delta-5 and delta-6 desaturase activities estimated by serum fatty acid ratios. J Lipid Res. 51, 2325-2333.
13. Schadt, E. E., Molony, C., Chudin, E., Hao, K., Yang, X., Lum, P. Y., Kasarskis, A., Zhang, B., Wang, S., Suver, C., et al. (2008). Mapping the genetic architecture of gene expression in human liver. PLoS Biol. 6, e107.
14. Pawar, A., Botolin, D., Mangelsdorf, D. J., and Jump, D. B. (2003). The role of liver X receptor-alpha in the fatty acid regulation of hepatic gene expression. J Biol Chem. 278, 40736-40743.
15. Matsuzaka, T., Shimano, H., Yahagi, N., Amemiya-Kudo, M., Yoshikawa, T., Hasty, A. H., Tamura, Y., Osuga, J., Okazaki, H., Iizuka, Y., et al. (2002). Dual regulation of mouse Delta(5)- and Delta(6)-desaturase gene expression by SREBP-1 and PPARalpha. J Lipid Res. 43, 107-114.
16. Stranger, B. E., Forrest, M. S., Dunning, M., Ingle, C. E., Beazley, C., Thorne, N., Redon, R., Bird, C. P., de Grassi, A., Lee, C., et al. (2007). Relative impact of nucleotide and copy number variation on gene expression phenotypes. Science. 315, 848-853.
17. Edgar, R., Domrachev, M., and Lash, A. E. (2002). Gene Expression Omnibus: NCBI gene expression and hybridization array data repository. Nucleic Acids Res. 30, 207-210.
18. Purcell, S., Neale, B., Todd-Brown, K., Thomas, L., Ferreira, M. A., Bender, D., Mailer, J., Sklar, P., de Bakker, P. I., Daly, M. J., et al. (2007). PLINK: a tool set for whole-genome association and population-based linkage analyses. Am J Hum Genet. 81, 559-575.

19. Barrett, J. C., Fry, B., Mailer, J., and Daly, M. J. (2005). Haploview: analysis and visualization of LD and haplotype maps. Bioinformatics. 21, 263-265.

20. Gabriel, S. B., Schaffner, S. F., Nguyen, H., Moore, J. M., Roy, J., Blumenstiel, B., Higgins, J., DeFelice, M., Lochner, A., Faggart, M., et al. (2002). The structure of haplotype blocks in the human genome. Science. 296, 2225-2229.

21. Frazer, K. A., Pachter, L., Poliakov, A., Rubin, E. M., and Dubchak, I. (2004). VISTA: computational tools for comparative genomics. Nucleic Acids Res. 32, W273-279.

22. Loots, G. G., Ovcharenko, I., Pachter, L., Dubchak, I., and Rubin, E. M. (2002). rVista for comparative sequence-based discovery of functional transcription factor binding sites. Genome Res. 12, 832-839.

23. Pfaffl, M. W. (2001). A new mathematical model for relative quantification in real-time RT-PCR. Nucleic Acids Res. 29, e45.

24. Marquardt, A., Stohr, H., White, K., and Weber, B. H. (2000). cDNA cloning, genomic structure, and chromosomal localization of three members of the human fatty acid desaturase family. Genomics. 66, 175-183.

25. Ueda, R., Iketaki, H., Nagata, K., Kimura, S., Gonzalez, F. J., Kusano, K., Yoshimura, T., and Yamazoe, Y. (2006). A common regulatory region functions bidirectionally in transcriptional activation of the human CYP1A1 and CYP1A2 genes. Mol Pharmacol. 69, 1924-1930.

26. Rise, P., Ghezzi, S., Carissimi, R., Mastromauro, F., Petroni, A., and Galli, C. (2007). Delta5 desaturase mRNA levels are increased by simvastatin via SREBP-1 at early stages, not via PPARalpha, in THP-1 cells. Eur J Pharmacol. 571, 97-105.

27. Repa, J. J., Liang, G., Ou, J., Bashmakov, Y., Lobaccaro, J. M., Shimomura, I., Shan, B., Brown, M. S., Goldstein, J. L., and Mangelsdorf, D. J. (2000). Regulation of mouse sterol regulatory element-binding protein-1c gene (SREBP-1c) by oxysterol receptors, LXRalpha and LXR-beta. Genes Dev. 14, 2819-2830.

28. Poudel-Tandukar, K., Nanri, A., Iwasaki, M., Mizoue, T., Matsushita, Y., Takahashi, Y., Noda, M., Inoue, M., and Tsugane, S. (2011). Long chain n-3 fatty acids intake, fish consumption and suicide in a cohort of Japanese men and women—the Japan Public Health Center-based (JPHC) prospective study. J Affect Disord. 129, 282-288.

29. Hibberd, C. M., Brooke, O. G., Carter, N. D., Haug, M., and Harzer, G. (1982). Variation in the composition of breast milk during the first 5 weeks of lactation: implications for the feeding of preterm infants. Arch Dis Child. 57, 658-662.

30. Mellies, M. J., Ishikawa, T. T., Gartside, P., Burton, K., MacGee, J., Allen, K., Steiner, P. M., Brady, D., and Glueck, C. J. (1978). Effects of varying maternal dietary cholesterol and phytosterol in lactating women and their infants. Am J Clin Nutr. 31, 1347-1354.

31. Potter, J. M., and Nestel, P. J. (1976). The effects of dietary fatty acids and cholesterol on the milk lipids of lactating women and the plasma cholesterol of breast-fed infants. Am J Clin Nutr. 29, 54-60.

32. Harris, J. I., Hibbeln, J. R., Mackey, R. H., and Muldoon, M. F. (2004). Statin treatment alters serum n-3 and n-6 fatty acids in hypercholesterolemic patients. Prostaglandins Leukot Essent Fatty Acids. 71, 263-269.

33. Jula, A., Marniemi, J., Ronnemaa, T., Virtanen, A., and Huupponen, R. (2005). Effects of diet and simvastatin on fatty acid composition in hypercholesterolemic men: a randomized controlled trial. Arterioscler Thromb Vasc Biol. 25, 1952-1959.

34. Studer, M., Briel, M., Leimenstoll, B., Glass, T. R., and Bucher, H. C. (2005). Effect of different antilipidemic agents and diets on mortality: a systematic review. Arch Intern Med. 165, 725-730.

35. Nakayama, K., Bayasgalan, T., Tazoe, F., Yanagisawa, Y., Gotoh, T., Yamanaka, K., Ogawa, A., Munkhtulga, L., Chimedregze, U., Kagawa, Y., et al. (2010). A single nucleotide polymorphism in the FADS1/FADS2 gene is associated with plasma lipid profiles in two genetically similar Asian ethnic groups with distinctive differences in lifestyle. Hum Genet. 127, 685-690.

36. Morales, E., Bustamante, M., Gonzalez, J. R., Guxens, M., Torrent, M., Mendez, M., Garcia-Esteban, R., Julvez, J., Forns, J., Vrijheid, M., et al. (2011). Genetic Variants of the FADS Gene Cluster and ELOVL Gene Family, Colostrums LC-PUFA Levels, Breastfeeding, and Child Cognition. PLoS One. 6, e17181.

37. Marquardt A, Stohr H, White K, Weber B H. cDNA cloning, genomic structure, and chromosomal localization of three members of the human fatty acid desaturase family. Genomics 2000; 66(2): 175-83.

38. Nakamura M T, Nara T Y. Structure, function, and dietary regulation of delta6, delta5, and delta9 desaturases. Annu Rev Nutr 2004; 24: 345-376.

39. Park W J, Kothapalli K S, Reardon H T, Kim L Y, Brenna J T. Novel fatty acid desaturase 3 (FADS3) transcripts generated by alternative splicing. Gene 2009; 446(1):28-34.

40. Park W J, Reardon H T, Tyburczy C, Kothapalli K S, Brenna J T. Alternative splicing generates a novel FADS2 alternative transcript in baboons. Mol Biol Rep 2010; 37(5):2403-6.

41. Park W J, Kothapalli K S, Reardon H T, Lawrence P, Qian S B, Brenna J T. A novel FADS1 isoform potentiates FADS2-mediated production of eicosanoid precursor fatty acids. J Lipid Res 2012; 53(8):1502-12.

42. Reardon H T, Zhang J, Kothapalli K S, Kim A J, Park W J, Brenna J T. Insertion-deletions in a FADS2 intron 1 conserved regulatory locus control expression of fatty acid desaturases 1 and 2 and modulate response to simvastatin. Prostaglandins Leukot Essent Fatty Acids 2012; 87(1): 25-33.

TABLE 1

Single Polymorphisms in FADS2 intron 1 significantly associated with FADS1 expression.

| polymorphism | Base position[a] | p-value | Beta[b] | Bonferroni[c] | FDR[d] |
|---|---|---|---|---|---|
| rs2845573 | 61358484 | 0.00073 | −0.21 | 0.0299 | 0.00597 |
| rs2727270 | 61359813 | 0.00073 | −0.21 | 0.0299 | 0.00597 |
| rs2727271 | 61359934 | 0.00065 | −0.21 | 0.0265 | 0.00597 |
| rs2524299 | 61361358 | 0.00053 | −0.23 | 0.0216 | 0.00597 |
| rs2072114 | 61361791 | 0.00073 | −0.21 | 0.0299 | 0.00597 |
| rs2851682 | 61372588 | 0.00091 | −0.21 | 0.0374 | 0.00623 |

[a]Base positions from NCBI Build 36
[b]Linear regression coefficient
[c]Bonferroni adjusted p-value
[d]False discovery rate (Benjamini-Hochberg method)

TABLE 2

Haplotype testing for association with FADS1 expression.

| Haplotype | Frequency | Beta[a] | p-value | Empirical p-value[b] |
|---|---|---|---|---|
| CACACATCGA | 0.67 | 0.090 | 0.061 | 0.15 |
| TTATAGACGG | 0.24 | −0.12 | 0.010 | 0.028 |
| CAAAAAATAA | 0.089 | 0.068 | 0.36 | 0.64 |

[a] Linear regression coefficient
[b] Corrected empirical p-value from max(T) permutation testing, controlling familywise error rate

TABLE 3

InDel Mutations near the putative SRE in FADS2 intron 1.

| ID number | Sequence | Distance to SRE (bp) | D/D haplotype |
|---|---|---|---|
| rs66698963 | -/ACTTCTCCCTGCCTCCCCAGGG | 137 | Deletion |
| rs138766446 or rs149597144 | -/CCA or -/A | 81 or 83 | Deletion |

What is claimed is:

1. A method of modulating total cholesterol, LDL, or C-reactive protein levels or treating coronary artery disease or atopic eczema in a human subject, comprising: obtaining a nucleic acid sample from the human subject; detecting whether Insertion I and Insertion II in intron 1 of the FADS2 gene are present in the nucleic acid sample; determining the need to treat the human subject with a FADS-modulating agent selected from a statin and an LXR agonist based on the detection of the absence of Insertion I and Insertion II in the nucleic acid sample; and administering a therapeutically effective amount of a statin or an LXR agonist to the human subject.

2. The method of claim 1, wherein the statin is selected from the group consisting of simvastatin, atorvastatin, mevacor, fluvastatin, lovastatin, pravastatin, and rosuvastatin.

3. The method of claim 1, wherein the LXR agonist is selected from the group consisting of GW3965, hypocholamide, T0901317, and N,N-dimethyl-3beta-hydroxy-cholenamide.

4. The method of claim 1, wherein the detecting step comprises amplification with a pair of isolated oligonucleotide 5' primer and 3' primer to produce an amplicon.

5. The method of claim 4, wherein the detecting step further comprises sequencing the amplicon or comparing the amplicon to a control amplicon having Insertion I or Insertion II to determine the size of the amplicon.

6. The method of claim 4,
wherein the 5' primer specifically hybridizes to a sequence antisense to SEQ ID NOs: 7, 10, 11 or 23;
wherein the 3' primer specifically hybridizes to a sequence of SEQ ID NO: 8;

wherein the 5' primer and the 3' primer are capable of amplifying at least partial intron 1 of the FADS2 gene indicative of presence or absence of Insertion I, and the length of the amplified sequence amplicon exceeds or equals to the combined lengths of the 5' primer and the 3' primer.

7. The method of claim 4,
wherein the 5' primer specifically hybridizes to a sequence antisense to SEQ ID NOs: 7 or 23;
wherein the 3' primer specifically hybridizes to a sequence of SEQ ID NOs: 8, 9, or 11;
wherein the 5' primer and the 3' primer are capable of amplifying at least partial intron 1 of the FADS2 gene indicative of presence or absence of Insertion I, and the length of the amplicon exceeds or equals to the combined lengths of the 5' primer and the 3' primer.

8. The method of claim 4,
wherein the 5' primer specifically hybridizes to a sequence antisense to SEQ ID NOs: 12, or 14;
wherein the 3' primer specifically hybridizes to a sequence of SEQ ID NOs: 13 or 23;
wherein the 5' primer and the 3' primer are capable of amplifying at least partial intron 1 of the FADS2 gene indicative of presence or absence of Insertion II, and the length of the amplicon exceeds or equals to the combined lengths of the 5' primer and the 3' primer.

9. The method of claim 4,
wherein the 5' primer specifically hybridizes to a sequence antisense to SEQ ID NO: 12;
wherein the 3' primer specifically hybridizes to a sequence of SEQ ID NOs: 13, 15 or 23;
wherein the 5' primer and the 3' primer are capable of amplifying at least partial intron 1 of the FADS2 gene indicative of presence or absence of Insertion II, and the length of the amplicon exceeds or equals to the combined lengths of the 5' primer and the 3' primer.

10. The method of claim 4, wherein the 3' end nucleotide of the 5' primer hybridizes to a nucleotide which is within the antisense sequence of Insertion I or Insertion II.

11. The method of claim 4, wherein the 3' end nucleotide of the 3' primer hybridizes to a nucleotide which is within the sequence of Insertion I or Insertion II.

12. The method of claim 10, wherein the 3' end nucleotide of the 5' primer does not form Watson-Crick base pair with the nucleotide if the intron 1 of the FADS2 gene to be amplified lacks Insertion I or Insertion II.

13. The method of claim 11, wherein the 3' end nucleotide of the 3' primer does not form Watson-Crick base pair with the nucleotide if the intron 1 of the FADS2 gene to be amplified lacks Insertion I or Insertion II.

* * * * *

SEQUENCE LISTING

<160> NUMBER OF SEQ ID NOS: 23

<210> SEQ ID NO 1
<211> LENGTH: 22
<212> TYPE: DNA
<213> ORGANISM: Homo sapiens

<400> SEQUENCE: 1
acttctccct gcctccccag gg                                              22

<210> SEQ ID NO 2
<211> LENGTH: 122
<212> TYPE: DNA
<213> ORGANISM: Homo sapiens

<400> SEQUENCE: 2
ccagggcctc ctccctgcct ccccagggac ttctccctgc ctccccaggg acttctccct      60
gcctccccag ggccctggaa tagcacgtct cttttccctg aaaatactct tgacctgatc     120
ct                                                                   122

<210> SEQ ID NO 3
<211> LENGTH: 100
<212> TYPE: DNA
<213> ORGANISM: Homo sapiens

<400> SEQUENCE: 3
ccagggcctc ctccctgcct ccccagggac ttctccctgc ctccccaggg ccctggaata      60
gcacgtctct tttccctgaa aatactcttg acctgatcct                           100

<210> SEQ ID NO 4
<211> LENGTH: 103
<212> TYPE: DNA
<213> ORGANISM: Homo sapiens

<400> SEQUENCE: 4
ccctgggctc ctccctgccc gcaccctggg cctcctccct gcctgccccc caccccagc       60

```
cctcctccct gcctgccccc agggcctcct ccctgcctcc cca                  103

<210> SEQ ID NO 5
<211> LENGTH: 100
<212> TYPE: DNA
<213> ORGANISM: Homo sapiens

<400> SEQUENCE: 5
ccctgggctc ctccctgccc gcaccctggg cctcctccct gcctgccccc cccagccct   60 cctccctgcc tgccccagg gcctcctccc tgcctcccca                        100

<210> SEQ ID NO 6
<211> LENGTH: 102
<212> TYPE: DNA
<213> ORGANISM: Homo sapiens

<400> SEQUENCE: 6
ccctgggctc ctccctgccc gcaccctggg cctcctccct gcctgccccc cccccagcc   60 ctcctccctg cctgcccca gggcctcctc cctgcctccc ca                     102

<210> SEQ ID NO 7
<211> LENGTH: 317
<212> TYPE: DNA
<213> ORGANISM: Homo sapiens

<400> SEQUENCE: 7 ttttctcaaag gccgtggtgt gatgtgagga ggaccaatga aggggctttt tcaggcccag   60
ccctgggccc tgactttggc agctcctccg ggcctctccc agggccttgc tcattttgca  120
taggcggctg aggctctggt ggggactgat caccccaccc agagccagca aagctggtca  180
ccactgcaac cctgggctcc tccctgcccg caccctgggc ctcctccctg cctgccccc   240 caccccagcc ctcctccctg cctgccccca gggcctcctc cctgcctccc cagggacttc  300
tccctgcctc cccaggg                                                317

<210> SEQ ID NO 8
<211> LENGTH: 290
<212> TYPE: DNA
<213> ORGANISM: Homo sapiens

<400> SEQUENCE: 8
ccctggaata gcacgtctct ttccctgaa aatactcttg acctgatcct ctgctaccat    60
cccttttcgg ctcggctagt gggtcacagg catttttaa gaaaccgtgg gcccagtttt  120
ctcctgcacg aagtgttgct ttgtcagtct gttctagaca caaatagaac aaagaccaag  180
caaaggactt gatgccagca atgcagtaag gagatgatgg gagactggca gttacccttg  240
ggagatcctt acgtgtgggg ctgaaaagat ttccaggagt ggttagcact             290

<210> SEQ ID NO 9
<211> LENGTH: 312
<212> TYPE: DNA
<213> ORGANISM: Homo sapiens

<400> SEQUENCE: 9 acttctcct gcctccccag ggccctggaa tagcacgtct cttttccctg aaaatactct    60
tgacctgatc ctctgctacc atcccttttc ggctcggcta gtgggtcaca ggcatttttt  120
aagaaaccgt gggcccagtt ttctcctgca cgaagtgttg ctttgtcagt ctgttctaga  180
```

```
cacaaataga acaaagacca agcaaaggac ttgatgccag caatgcagta aggagatgat      240
gggagactgg cagttaccct tgggagatcc ttacgtgtgg ggctgaaaag atttccagga      300
gtggttagca ct                                                          312

<210> SEQ ID NO 10
<211> LENGTH: 339
<212> TYPE: DNA
<213> ORGANISM: Homo sapiens

<400> SEQUENCE: 10
tttctcaaag gccgtggtgt gatgtgagga ggaccaatga aggggctttt tcaggcccag       60
ccctgggccc tgactttggc agctcctccg ggcctctccc agggccttgc tcattttgca      120
taggcggctg aggctctggt ggggactgat caccccaccc agagccagca aagctggtca      180
ccactgcaac cctgggctcc tccctgcccg caccctgggc ctcctccctg cctgccccc       240 caccccagcc ctcctccctg cctgccccca gggcctcctc cctgcctccc cagggacttc      300
tccctgcctc cccagggact tctccctgcc tccccaggg                             339

<210> SEQ ID NO 11
<211> LENGTH: 22
<212> TYPE: DNA
<213> ORGANISM: Homo sapiens

<400> SEQUENCE: 11
acttctccct gcctccccag gg                                                22

<210> SEQ ID NO 12
<211> LENGTH: 239
<212> TYPE: DNA
<213> ORGANISM: Homo sapiens

<400> SEQUENCE: 12
tttctcaaag gccgtggtgt gatgtgagga ggaccaatga aggggctttt tcaggcccag       60
ccctgggccc tgactttggc agctcctccg ggcctctccc agggccttgc tcattttgca      120
taggcggctg aggctctggt ggggactgat caccccaccc agagccagca aagctggtca      180
ccactgcaac cctgggctcc tccctgcccg caccctgggc ctcctccctg cctgccccc       239

<210> SEQ ID NO 13
<211> LENGTH: 387
<212> TYPE: DNA
<213> ORGANISM: Homo sapiens

<400> SEQUENCE: 13
ccccagccct cctccctgcc tgccccagg gcctcctccc tgcctcccca gggacttctc        60
cctgcctccc cagggacttc tccctgcctc cccagggccc tggaatagca cgtctctttt      120
ccctgaaaat actcttgacc tgatcctctg ctaccatccc ttttcggctc ggctagtggg      180
tcacaggcat ttttttaagaa accgtgggcc cagttttctc ctgcacgaag tgttgctttg     240
tcagtctgtt ctagacacaa atagaacaaa gaccaagcaa aggacttgat gccagcaatg      300
cagtaaggag atgatgggag actggcagtt acccttggga gatccttacg tgtgggctg      360 aaaagatttc caggagtggt tagcact                                          387

<210> SEQ ID NO 14
<211> LENGTH: 242
<212> TYPE: DNA
<213> ORGANISM: Homo sapiens
```

```
<400> SEQUENCE: 14
tttctcaaag gccgtggtgt gatgtgagga ggaccaatga aggggctttt tcaggcccag      60
ccctgggccc tgactttggc agctcctccg ggcctctccc agggccttgc tcattttgca     120
taggcggctg aggctctggt ggggactgat caccccaccc agagccagca aagctggtca     180
ccactgcaac cctgggctcc tccctgcccg caccctgggc ctcctccctg cctgcccccc     240
ca                                                                    242

<210> SEQ ID NO 15
<211> LENGTH: 390
<212> TYPE: DNA
<213> ORGANISM: Homo sapiens

<400> SEQUENCE: 15 ccacccagc cctcctccct gcctgccccc agggcctcct ccctgcctcc ccagggactt       60
ctccctgcct cccagggac ttctccctgc ctccccaggg cctggaata gcacgtctct       120 tttccctgaa atactcttg acctgatcct ctgctaccat cccttttcgg ctcggctagt      180
gggtcacagg cattttttaa gaaaccgtgg gcccagtttt ctcctgcacg aagtgttgct     240
ttgtcagtct gttctagaca caaatagaac aaagaccaag caaggactt gatgccagca      300 atgcagtaag gagatgatgg gagactggca gttacccttg ggagatcctt acgtgtgggg     360
ctgaaaagat ttccaggagt ggttagcact                                      390

<210> SEQ ID NO 16
<211> LENGTH: 241
<212> TYPE: DNA
<213> ORGANISM: Homo sapiens

<400> SEQUENCE: 16
tttctcaaag gccgtggtgt gatgtgagga ggaccaatga aggggctttt tcaggcccag      60
ccctgggccc tgactttggc agctcctccg ggcctctccc agggccttgc tcattttgca     120
taggcggctg aggctctggt ggggactgat caccccaccc agagccagca aagctggtca     180
ccactgcaac cctgggctcc tccctgcccg caccctgggc ctcctccctg cctgcccccc     240
c                                                                     241

<210> SEQ ID NO 17
<211> LENGTH: 387
<212> TYPE: DNA
<213> ORGANISM: Homo sapiens

<400> SEQUENCE: 17
ccccagccct cctcctgcc tgccccagg gcctcctccc tgcctcccca gggacttctc        60
cctgcctccc cagggacttc tccctgcctc ccagggccc tggaatagca cgtctctttt      120
ccctgaaaat actcttgacc tgatcctctg ctaccatc ttttcggctc ggctagtggg       180
tcacaggcat ttttttaagaa accgtgggcc cagttttctc ctgcacgaag tgttgctttg    240
tcagtctgtt ctagacacaa atagaacaaa gaccaagcaa aggacttgat gccagcaatg     300
cagtaaggag atgatgggag actggcagtt acccttggga gatccttacg tgtgggctg      360 aaaagatttc aggagtggt tagcact                                          387

<210> SEQ ID NO 18
<211> LENGTH: 242
<212> TYPE: DNA
```

<213> ORGANISM: Homo sapiens

<400> SEQUENCE: 18

```
tttctcaaag gccgtggtgt gatgtgagga ggaccaatga aggggctttt tcaggcccag    60
ccctgggccc tgactttggc agctcctccg ggcctctccc agggccttgc tcattttgca   120
taggcggctg aggctctggt ggggactgat caccccaccc agagccagca aagctggtca   180
ccactgcaac cctgggctcc tccctgcccg caccctgggc ctcctccctg cctgccccca   240
ca                                                                 242
```

<210> SEQ ID NO 19
<211> LENGTH: 388
<212> TYPE: DNA
<213> ORGANISM: Homo sapiens

<400> SEQUENCE: 19

```
accccagccc tcctccctgc ctgcccccag ggcctcctcc ctgcctcccc agggacttct    60
ccctgcctcc ccagggactt ctccctgcct cccagggggcc ctggaatagc acgtctcttt   120
tccctgaaaa tactcttgac ctgatcctct gctaccatcc cttttcggct cggctagtgg   180
gtcacaggca ttttttaaga aaccgtgggc ccagttttct cctgcacgaa gtgttgcttt   240
gtcagtctgt tctagacaca aatagaacaa agaccaagca aaggacttga tgccagcaat   300
gcagtaagga gatgatggga gactggcagt taccccttggg agatccttac gtgtgggct    360
gaaaagattt ccaggagtgg ttagcact                                      388
```

<210> SEQ ID NO 20
<211> LENGTH: 629
<212> TYPE: DNA
<213> ORGANISM: Homo sapiens

<400> SEQUENCE: 20

```
tttctcaaag gccgtggtgt gatgtgagga ggaccaatga aggggctttt tcaggcccag    60
ccctgggccc tgactttggc agctcctccg ggcctctccc agggccttgc tcattttgca   120
taggcggctg aggctctggt ggggactgat caccccaccc agagccagca aagctggtca   180
ccactgcaac cctgggctcc tccctgcccg caccctgggc ctcctccctg cctgccccca   240
caccccagcc ctcctccctg cctgccccca gggcctcctc cctgcctccc agggacttc    300
tccctgcctc cccagggact ctccctgcct ccccagggc cctggaatag cacgtctctt   360
ttccctgaaa atactcttga cctgatcctc tgctaccatc ccttttcggc tcggctagtg   420
ggtcacaggc attttttaag aaaccgtggg cccagttttc tcctgcacga agtgttgctt   480
tgtcagtctg ttctagacac aaatagaaca agaccaagc aaaggacttg atgccagcaa   540
tgcagtaagg agatgatggg agactggcag ttacccttgg gagatcctta cgtgtgggc    600
tgaaaagatt ccaggagtg gttagcact                                      629
```

<210> SEQ ID NO 21
<211> LENGTH: 604
<212> TYPE: DNA
<213> ORGANISM: Homo sapiens

<400> SEQUENCE: 21

```
tttctcaaag gccgtggtgt gatgtgagga ggaccaatga aggggctttt tcaggcccag    60
ccctgggccc tgactttggc agctcctccg ggcctctccc agggccttgc tcattttgca   120
taggcggctg aggctctggt ggggactgat caccccaccc agagccagca aagctggtca   180
```

```
ccactgcaac cctgggctcc tccctgcccg caccctgggc ctcctccctg cctgccccc    240 cccagccctc ctccctgcct gccccaggg cctcctccct gcctcccag ggacttctcc    300 ctgcctcccc agggcctgg aatagcacgt ctcttttccc tgaaaatact cttgacctga    360
tcctctgcta ccatccctt tcggctcggc tagtgggtca caggcatttt ttaagaaacc    420
gtgggcccag ttttctcctg cacgaagtgt tgctttgtca gtctgttcta gacacaaata    480
gaacaaagac caagcaaagg acttgatgcc agcaatgcag taaggagatg atgggagact    540
ggcagttacc cttgggagat ccttacgtgt ggggctgaaa agatttccag gagtggttag    600
cact                                                                604

<210> SEQ ID NO 22
<211> LENGTH: 606
<212> TYPE: DNA
<213> ORGANISM: Homo sapiens

<400> SEQUENCE: 22
tttctcaaag gccgtggtgt gatgtgagga ggaccaatga aggggctttt tcaggcccag     60
ccctgggccc tgactttggc agctcctccg ggcctctccc agggccttgc tcattttgca    120
taggcggctg aggctctggt ggggactgat caccccaccc agagccagca aagctggtca    180
ccactgcaac cctgggctcc tccctgcccg caccctgggc ctcctccctg cctgccccc    240 ccccagccc tcctccctgc ctgccccag ggcctcctcc ctgcctcccc agggacttct    300
ccctgcctcc ccagggccct ggaatagcac gtctcttttc cctgaaaata ctcttgacct    360
gatcctctgc taccatccct tttcggctcg gctagtgggt cacaggcatt ttttaagaaa    420
ccgtgggccc agttttctcc tgcacgaagt gttgctttgt cagtctgttc tagacacaaa    480
tagaacaaag accaagcaaa ggacttgatg ccagcaatgc agtaaggaga tgatgggaga    540
ctggcagtta cccttgggag atccttacgt gtggggctga aaagatttcc aggagtggtt    600
agcact                                                              606

<210> SEQ ID NO 23
<211> LENGTH: 75
<212> TYPE: DNA
<213> ORGANISM: Homo sapiens

<400> SEQUENCE: 23
ccccagccct cctccctgcc tgccccagg gcctcctccc tgcctcccca gggacttctc     60
cctgcctccc caggg                                                     75
```